(12) United States Patent
Kerr et al.

(10) Patent No.: US 11,464,631 B2
(45) Date of Patent: Oct. 11, 2022

(54) METHODS AND SYSTEMS FOR RAPID RETRACTION OF A TRANSCATHETER HEART VALVE DELIVERY SYSTEM

(71) Applicant: Neovasc Tiara Inc., Richmond (CA)

(72) Inventors: Ian Fraser Kerr, Vancouver (CA); Karen Tsoek-Ji Wong, Richmond (CA); Colin Alexander Nyuli, Vancouver (CA); Randy Matthew Lane, Langley (CA)

(73) Assignee: Neovasc Tiara Inc., Richmond (CA)

( * ) Notice: Subject to any disclaimer, the term of this patent is extended or adjusted under 35 U.S.C. 154(b) by 299 days.

(21) Appl. No.: 16/796,157

(22) Filed: Feb. 20, 2020

(65) Prior Publication Data

US 2020/0188105 A1 Jun. 18, 2020

Related U.S. Application Data

(63) Continuation of application No. 15/819,512, filed on Nov. 21, 2017, now abandoned.

(60) Provisional application No. 62/424,910, filed on Nov. 21, 2016.

(51) Int. Cl.
  *A61F 2/24* (2006.01)
  *A61M 29/02* (2006.01)
  *A61F 2/95* (2013.01)

(52) U.S. Cl.
  CPC .......... *A61F 2/2433* (2013.01); *A61F 2/2427* (2013.01); *A61F 2/2436* (2013.01); *A61M 29/02* (2013.01); *A61F 2/9517* (2020.05); *A61F 2250/0064* (2013.01)

(58) Field of Classification Search
  CPC ........ A61F 2/95; A61F 2/2433; A61F 2/2427; A61F 2/2436; A61M 29/02
  See application file for complete search history.

(56) References Cited

U.S. PATENT DOCUMENTS

| 2,967,856 A | 1/1961 | Coover, Jr. et al. |
| 8,579,964 B2 | 11/2013 | Lane et al. |
| 2007/0168014 A1 | 7/2007 | Jimenez et al. |

(Continued)

FOREIGN PATENT DOCUMENTS

| CA | 2874219 C | 7/2020 |
| CN | 109996581 A | 7/2019 |

(Continued)

OTHER PUBLICATIONS

"U.S. Appl. No. 15/819,512, Non Final Office Action dated Nov. 22, 2019", 15 pgs.

(Continued)

*Primary Examiner* — Tuan V Nguyen
(74) *Attorney, Agent, or Firm* — Schwegman Lundberg & Woessner, P.A.

(57) ABSTRACT

Methods for the rapid retraction of trans-catheter heart valve delivery systems are provided. A rapid retraction trans-catheter heart valve delivery system comprises a catheter based delivery system. The delivery system has internal mechanisms that allow for the controlled deployment of a heart valve prosthesis, as well as mechanisms that allow for quickly closing the catheter once the heart valve prosthesis has been implanted. This rapid retraction ability allows for reduced procedural durations and thus reduced risk to the patient.

10 Claims, 15 Drawing Sheets

(56) References Cited

U.S. PATENT DOCUMENTS

| | | | |
|---|---|---|---|
| 2009/0254165 A1* | 10/2009 | Tabor | A61F 2/844 623/1.11 |
| 2011/0015616 A1* | 1/2011 | Straubinger | A61F 2/2427 604/528 |
| 2011/0264191 A1* | 10/2011 | Rothstein | A61F 2/2436 623/1.11 |
| 2011/0319989 A1* | 12/2011 | Lane | A61F 2/2418 623/2.37 |
| 2012/0179243 A1 | 7/2012 | Yang et al. | |
| 2013/0231735 A1 | 9/2013 | Deem et al. | |
| 2013/0297011 A1* | 11/2013 | Morris | A61F 2/2436 623/2.11 |
| 2014/0067050 A1 | 3/2014 | Costello et al. | |
| 2015/0134054 A1* | 5/2015 | Morrissey | A61F 2/2436 623/2.11 |
| 2015/0297378 A1 | 10/2015 | Senness et al. | |
| 2015/0306358 A1 | 10/2015 | Duffy et al. | |
| 2018/0140419 A1 | 5/2018 | Kerr et al. | |

FOREIGN PATENT DOCUMENTS

| | | |
|---|---|---|
| CN | 109996581 B | 10/2021 |
| CN | 113893064 A | 1/2022 |
| DE | 10103955 B4 | 11/2001 |
| DE | 10033858 B4 | 1/2002 |
| DE | 102005052628 A1 | 5/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 202013011734 U1 | 4/2014 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |
| EP | 1212011 B1 | 11/2006 |
| EP | 1261294 B1 | 11/2006 |
| EP | 1318775 B1 | 11/2006 |
| EP | 1429690 B1 | 11/2006 |
| EP | 1173111 B1 | 12/2006 |
| EP | 1239795 B1 | 12/2006 |
| EP | 1299049 B1 | 12/2006 |
| EP | 1487382 B1 | 12/2006 |
| EP | 1112044 B1 | 1/2007 |
| EP | 1482997 B1 | 1/2007 |
| EP | 1117352 B1 | 2/2007 |
| EP | 1128849 B1 | 2/2007 |
| EP | 1392666 B1 | 2/2007 |
| EP | 1474077 B1 | 2/2007 |
| EP | 1251805 B1 | 3/2007 |
| EP | 1117334 B1 | 4/2007 |
| EP | 1263484 B1 | 5/2007 |
| EP | 1313410 B1 | 5/2007 |
| EP | 1370200 B1 | 5/2007 |
| EP | 1560526 B1 | 6/2007 |
| EP | 1173117 B1 | 7/2007 |
| EP | 1434615 B1 | 7/2007 |
| EP | 1465546 B1 | 7/2007 |
| EP | 1499366 B1 | 7/2007 |
| EP | 1225948 B1 | 8/2007 |
| EP | 1519962 B1 | 9/2007 |
| EP | 1337285 B1 | 10/2007 |
| EP | 1112042 B1 | 11/2007 |
| EP | 1148821 B1 | 11/2007 |
| EP | 1143882 B1 | 12/2007 |
| EP | 1330189 B1 | 12/2007 |
| EP | 1489996 B1 | 12/2007 |
| EP | 1296618 B1 | 1/2008 |

(56) References Cited

FOREIGN PATENT DOCUMENTS

| | | |
|---|---|---|
| EP | 1401356 B1 | 1/2008 |
| EP | 1629795 B1 | 1/2008 |
| EP | 1128786 B1 | 2/2008 |
| EP | 1616532 B1 | 2/2008 |
| EP | 1289447 B1 | 3/2008 |
| EP | 1895942 A2 | 3/2008 |
| EP | 1115353 B1 | 5/2008 |
| EP | 1330190 B1 | 5/2008 |
| EP | 1383448 B1 | 6/2008 |
| EP | 1251804 B1 | 7/2008 |
| EP | 1294310 B1 | 7/2008 |
| EP | 1313409 B1 | 7/2008 |
| EP | 1395202 B1 | 7/2008 |
| EP | 1395204 B1 | 7/2008 |
| EP | 1395205 B1 | 7/2008 |
| EP | 1423066 B1 | 7/2008 |
| EP | 1560545 B1 | 7/2008 |
| EP | 1605871 B1 | 7/2008 |
| EP | 1671608 B1 | 7/2008 |
| EP | 1690515 B1 | 7/2008 |
| EP | 1180987 B1 | 8/2008 |
| EP | 1337386 B1 | 8/2008 |
| EP | 1492579 B1 | 9/2008 |
| EP | 1524942 B1 | 9/2008 |
| EP | 1627091 B1 | 9/2008 |
| EP | 1827577 B1 | 9/2008 |
| EP | 1259195 B1 | 10/2008 |
| EP | 1704834 B1 | 10/2008 |
| EP | 1146835 B1 | 11/2008 |
| EP | 1498086 B1 | 11/2008 |
| EP | 1622548 B1 | 11/2008 |
| EP | 1235537 B1 | 12/2008 |
| EP | 1237509 B1 | 12/2008 |
| EP | 1355590 B1 | 12/2008 |
| EP | 1455680 B1 | 12/2008 |
| EP | 1472995 B1 | 12/2008 |
| EP | 1513474 B1 | 12/2008 |
| EP | 1562522 B1 | 12/2008 |
| EP | 1620042 B1 | 12/2008 |
| EP | 1690514 B1 | 12/2008 |
| EP | 1258232 B1 | 1/2009 |
| EP | 1420723 B1 | 1/2009 |
| EP | 1570809 B1 | 1/2009 |
| EP | 1395182 B1 | 2/2009 |
| EP | 1408882 B1 | 2/2009 |
| EP | 1482868 B1 | 2/2009 |
| EP | 1255510 B3 | 3/2009 |
| EP | 1330213 B1 | 3/2009 |
| EP | 1429651 B1 | 3/2009 |
| EP | 1610727 B1 | 4/2009 |
| EP | 1617788 B1 | 4/2009 |
| EP | 1634547 B1 | 4/2009 |
| EP | 1790318 B1 | 4/2009 |
| EP | 2040645 A1 | 4/2009 |
| EP | 1250165 B1 | 5/2009 |
| EP | 1842508 B1 | 6/2009 |
| EP | 1968482 B1 | 6/2009 |
| EP | 2072027 A1 | 6/2009 |
| EP | 1343438 B1 | 7/2009 |
| EP | 1406608 B1 | 7/2009 |
| EP | 1509256 B1 | 7/2009 |
| EP | 1626681 B1 | 7/2009 |
| EP | 1723935 B1 | 7/2009 |
| EP | 1803420 B1 | 7/2009 |
| EP | 2073755 A2 | 7/2009 |
| EP | 1401359 B1 | 8/2009 |
| EP | 1411865 B1 | 8/2009 |
| EP | 1485033 B1 | 8/2009 |
| EP | 1581120 B1 | 8/2009 |
| EP | 1620040 B1 | 8/2009 |
| EP | 1684667 B1 | 8/2009 |
| EP | 1872743 B1 | 8/2009 |
| EP | 1100378 B1 | 9/2009 |
| EP | 1198203 B1 | 9/2009 |
| EP | 1370201 B1 | 9/2009 |
| EP | 1408850 B1 | 9/2009 |
| EP | 1478364 B1 | 9/2009 |
| EP | 1653888 B1 | 9/2009 |
| EP | 1785154 B1 | 9/2009 |
| EP | 1881804 B1 | 9/2009 |
| EP | 1903991 B1 | 9/2009 |
| EP | 1418865 B1 | 10/2009 |
| EP | 1561437 B1 | 10/2009 |
| EP | 1615595 B1 | 10/2009 |
| EP | 1353612 B1 | 11/2009 |
| EP | 1348406 B1 | 12/2009 |
| EP | 1370202 B1 | 12/2009 |
| EP | 1603492 B1 | 12/2009 |
| EP | 1670364 B1 | 12/2009 |
| EP | 1759663 B1 | 12/2009 |
| EP | 1994887 B1 | 12/2009 |
| EP | 1615593 B1 | 1/2010 |
| EP | 1643938 B1 | 1/2010 |
| EP | 1863402 B1 | 1/2010 |
| EP | 1943942 B1 | 1/2010 |
| EP | 2010101 B1 | 1/2010 |
| EP | 2081518 B1 | 1/2010 |
| EP | 1703865 B1 | 2/2010 |
| EP | 1276437 B1 | 3/2010 |
| EP | 1276439 B1 | 3/2010 |
| EP | 1411867 B1 | 3/2010 |
| EP | 1458313 B1 | 3/2010 |
| EP | 1520519 B1 | 3/2010 |
| EP | 1648340 B1 | 3/2010 |
| EP | 1682048 B1 | 3/2010 |
| EP | 1773239 B1 | 3/2010 |
| EP | 1935377 B1 | 3/2010 |
| EP | 1994912 B1 | 3/2010 |
| EP | 1154738 B1 | 4/2010 |
| EP | 1531762 B1 | 4/2010 |
| EP | 1600178 B1 | 4/2010 |
| EP | 1626682 B1 | 4/2010 |
| EP | 1511445 B1 | 5/2010 |
| EP | 1198213 B1 | 6/2010 |
| EP | 1250097 B1 | 6/2010 |
| EP | 1272249 B1 | 6/2010 |
| EP | 1978895 B1 | 6/2010 |
| EP | 1572033 B1 | 7/2010 |
| EP | 1968491 B1 | 7/2010 |
| EP | 2019652 B1 | 7/2010 |
| EP | 1610722 B1 | 8/2010 |
| EP | 1682047 B1 | 8/2010 |
| EP | 1952772 B1 | 8/2010 |
| EP | 1427356 B1 | 9/2010 |
| EP | 1765224 B1 | 9/2010 |
| EP | 1871290 B1 | 9/2010 |
| EP | 1895288 B1 | 9/2010 |
| EP | 1895913 B1 | 9/2010 |
| EP | 2014257 B1 | 9/2010 |
| EP | 163121881 | 9/2010 |
| EP | 1176913 B1 | 10/2010 |
| EP | 1178758 B1 | 10/2010 |
| EP | 1248579 B1 | 10/2010 |
| EP | 1913899 B1 | 10/2010 |
| EP | 1259193 B1 | 11/2010 |
| EP | 1928357 B1 | 11/2010 |
| EP | 1968660 B1 | 11/2010 |
| EP | 2249711 A2 | 11/2010 |
| EP | 1408895 B1 | 12/2010 |
| EP | 1465554 B1 | 12/2010 |
| EP | 1732473 B1 | 12/2010 |
| EP | 1827314 B1 | 12/2010 |
| EP | 1940321 B1 | 12/2010 |
| EP | 1964532 B1 | 12/2010 |
| EP | 2078498 B1 | 12/2010 |
| EP | 17688610 B1 | 12/2010 |
| EP | 1600182 B1 | 1/2011 |
| EP | 1617789 B1 | 1/2011 |
| EP | 1663332 B1 | 1/2011 |
| EP | 2147659 B1 | 1/2011 |
| EP | 2268231 A2 | 1/2011 |
| EP | 2273951 A1 | 1/2011 |
| EP | 1187582 B1 | 2/2011 |
| EP | 1450733 B1 | 2/2011 |

(56) References Cited

FOREIGN PATENT DOCUMENTS

| | | | |
|---|---|---|---|
| EP | 1803421 | B1 | 2/2011 |
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |
| EP | 2299938 | A2 | 3/2011 |
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |
| EP | 2055266 | B1 | 2/2012 |
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A1 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2520249 | A1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |
| EP | 2079400 | B1 | 1/2013 |
| EP | 2238947 | B1 | 1/2013 |
| EP | 2241287 | B1 | 1/2013 |
| EP | 2359774 | B1 | 1/2013 |
| EP | 2538878 | A1 | 1/2013 |
| EP | 2538883 | A1 | 1/2013 |
| EP | 1512383 | B1 | 2/2013 |
| EP | 1578474 | B1 | 2/2013 |
| EP | 1648339 | B1 | 2/2013 |
| EP | 1750622 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |

(56) References Cited

FOREIGN PATENT DOCUMENTS

| | | | |
|---|---|---|---|
| EP | 1977719 | B1 | 7/2013 |
| EP | 2111337 | B1 | 7/2013 |
| EP | 2298237 | B1 | 7/2013 |
| EP | 2309949 | B1 | 7/2013 |
| EP | 2608741 | A2 | 7/2013 |
| EP | 2611388 | A2 | 7/2013 |
| EP | 2611389 | A2 | 7/2013 |
| EP | 2618781 | A2 | 7/2013 |
| EP | 1599151 | B1 | 8/2013 |
| EP | 1761211 | B1 | 8/2013 |
| EP | 2047871 | B1 | 8/2013 |
| EP | 2142144 | B1 | 8/2013 |
| EP | 2150206 | B1 | 8/2013 |
| EP | 2319459 | B1 | 8/2013 |
| EP | 2397108 | B1 | 8/2013 |
| EP | 2623068 | A1 | 8/2013 |
| EP | 1758523 | B1 | 9/2013 |
| EP | 1545392 | B1 | 10/2013 |
| EP | 1638627 | B1 | 10/2013 |
| EP | 1779868 | B1 | 10/2013 |
| EP | 2073756 | B1 | 10/2013 |
| EP | 2111190 | B1 | 10/2013 |
| EP | 1848375 | B1 | 11/2013 |
| EP | 1928356 | B1 | 11/2013 |
| EP | 1933766 | B1 | 11/2013 |
| EP | 2109417 | B1 | 11/2013 |
| EP | 2194925 | B1 | 11/2013 |
| EP | 2387977 | B1 | 11/2013 |
| EP | 2476394 | B1 | 11/2013 |
| EP | 2529701 | B1 | 11/2013 |
| EP | 1945142 | B1 | 12/2013 |
| EP | 2387972 | B1 | 12/2013 |
| EP | 2477555 | B1 | 12/2013 |
| EP | 2670349 | A2 | 12/2013 |
| EP | 2117476 | B1 | 1/2014 |
| EP | 2526895 | B1 | 1/2014 |
| EP | 2526899 | B1 | 1/2014 |
| EP | 2529696 | B1 | 1/2014 |
| EP | 2529697 | B1 | 1/2014 |
| EP | 2529698 | B1 | 1/2014 |
| EP | 2529699 | B1 | 1/2014 |
| EP | 2679198 | A1 | 1/2014 |
| EP | 1395214 | B1 | 2/2014 |
| EP | 1499266 | B1 | 2/2014 |
| EP | 1838241 | B1 | 2/2014 |
| EP | 2520250 | B1 | 2/2014 |
| EP | 2526977 | B1 | 2/2014 |
| EP | 2693985 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |
| EP | 1804860 | B1 | 4/2014 |
| EP | 1926455 | B1 | 4/2014 |
| EP | 2081519 | B1 | 4/2014 |
| EP | 2117477 | B1 | 4/2014 |
| EP | 2405966 | B1 | 4/2014 |
| EP | 2420205 | B1 | 4/2014 |
| EP | 2593048 | B1 | 4/2014 |
| EP | 2713894 | A2 | 4/2014 |
| EP | 2713955 | A2 | 4/2014 |
| EP | 2723273 | A2 | 4/2014 |
| EP | 1499265 | B1 | 5/2014 |
| EP | 1594569 | B1 | 5/2014 |
| EP | 2029056 | B1 | 5/2014 |
| EP | 2257243 | B1 | 5/2014 |
| EP | 1791500 | B1 | 6/2014 |
| EP | 2073753 | B1 | 6/2014 |
| EP | 2306933 | B1 | 6/2014 |
| EP | 2331017 | B1 | 6/2014 |
| EP | 2337522 | B1 | 6/2014 |
| EP | 2389897 | B1 | 6/2014 |
| EP | 2606723 | B1 | 6/2014 |
| EP | 2739250 | A1 | 6/2014 |
| EP | 1487350 | B1 | 7/2014 |
| EP | 1977718 | B1 | 7/2014 |
| EP | 2117469 | B1 | 7/2014 |
| EP | 2124826 | B1 | 7/2014 |
| EP | 2258316 | B1 | 7/2014 |
| EP | 2747708 | A1 | 7/2014 |
| EP | 2750630 | A1 | 7/2014 |
| EP | 2750631 | A1 | 7/2014 |
| EP | 1667604 | B1 | 8/2014 |
| EP | 1786368 | B1 | 8/2014 |
| EP | 2211779 | B1 | 8/2014 |
| EP | 2217174 | B1 | 8/2014 |
| EP | 2293740 | B1 | 8/2014 |
| EP | 2367504 | B1 | 8/2014 |
| EP | 2453942 | B1 | 8/2014 |
| EP | 2475328 | B1 | 8/2014 |
| EP | 2545884 | B1 | 8/2014 |
| EP | 2571460 | B1 | 8/2014 |
| EP | 2763708 | A2 | 8/2014 |
| EP | 2765954 | A1 | 8/2014 |
| EP | 1935378 | B1 | 9/2014 |
| EP | 2246011 | B1 | 9/2014 |
| EP | 2422749 | B1 | 9/2014 |
| EP | 2531139 | B1 | 9/2014 |
| EP | 2609893 | B1 | 9/2014 |
| EP | 2777616 | A1 | 9/2014 |
| EP | 2779945 | A1 | 9/2014 |
| EP | 1853199 | B1 | 10/2014 |
| EP | 2133039 | B1 | 10/2014 |
| EP | 2549955 | B1 | 10/2014 |
| EP | 2549956 | B1 | 10/2014 |
| EP | 2651335 | B1 | 10/2014 |
| EP | 2785281 | A1 | 10/2014 |
| EP | 2793743 | A1 | 10/2014 |
| EP | 2793752 | A1 | 10/2014 |
| EP | 2049721 | B1 | 11/2014 |
| EP | 2142143 | B1 | 11/2014 |
| EP | 2229921 | B1 | 11/2014 |
| EP | 2288403 | B1 | 11/2014 |
| EP | 2415421 | B1 | 11/2014 |
| EP | 1551274 | B1 | 12/2014 |
| EP | 1768735 | B1 | 12/2014 |
| EP | 1959865 | B1 | 12/2014 |
| EP | 2077718 | B1 | 12/2014 |
| EP | 2303185 | B1 | 12/2014 |
| EP | 2334857 | B1 | 12/2014 |
| EP | 2365840 | B1 | 12/2014 |
| EP | 2420207 | B1 | 12/2014 |
| EP | 2422750 | B1 | 12/2014 |
| EP | 2707073 | B1 | 12/2014 |
| EP | 1768630 | B1 | 1/2015 |
| EP | 2254515 | B1 | 1/2015 |
| EP | 2641569 | B1 | 1/2015 |
| EP | 2709559 | B1 | 1/2015 |
| EP | 2825203 | A1 | 1/2015 |
| EP | 1903990 | B1 | 2/2015 |
| EP | 2255753 | B1 | 2/2015 |
| EP | 2335649 | B1 | 2/2015 |
| EP | 2522308 | B1 | 2/2015 |
| EP | 2591754 | B1 | 2/2015 |
| EP | 2835112 | A1 | 2/2015 |
| EP | 1861045 | B1 | 3/2015 |
| EP | 2029057 | B1 | 3/2015 |
| EP | 2193761 | B1 | 3/2015 |
| EP | 2379010 | B1 | 3/2015 |
| EP | 2416737 | B1 | 3/2015 |
| EP | 2298252 | B1 | 4/2015 |
| EP | 2536359 | B1 | 4/2015 |
| EP | 2538879 | B1 | 4/2015 |
| EP | 2609894 | B1 | 4/2015 |
| EP | 2693984 | B1 | 4/2015 |
| EP | 2712633 | B1 | 4/2015 |
| EP | 2747707 | B1 | 4/2015 |
| EP | 2862546 | A1 | 4/2015 |
| EP | 2863842 | A1 | 4/2015 |
| EP | 179149581 | | 4/2015 |
| EP | 1465555 | B1 | 5/2015 |

(56) References Cited

FOREIGN PATENT DOCUMENTS

| | | | |
|---|---|---|---|
| EP | 1924224 | B1 | 5/2015 |
| EP | 1992369 | B1 | 5/2015 |
| EP | 2410947 | B1 | 5/2015 |
| EP | 2484311 | B1 | 5/2015 |
| EP | 2654616 | B1 | 5/2015 |
| EP | 2866741 | A1 | 5/2015 |
| EP | 1646332 | B1 | 6/2015 |
| EP | 2745805 | B1 | 6/2015 |
| EP | 2749254 | B1 | 6/2015 |
| EP | 2877123 | A2 | 6/2015 |
| EP | 2882374 | A1 | 6/2015 |
| EP | 2884906 | A1 | 6/2015 |
| EP | 1729685 | B1 | 7/2015 |
| EP | 1976439 | B1 | 7/2015 |
| EP | 2068767 | B1 | 7/2015 |
| EP | 2068769 | B1 | 7/2015 |
| EP | 2444031 | B1 | 7/2015 |
| EP | 2455041 | B1 | 7/2015 |
| EP | 2498719 | B1 | 7/2015 |
| EP | 2558030 | B1 | 7/2015 |
| EP | 2752209 | B1 | 7/2015 |
| EP | 2892467 | A1 | 7/2015 |
| EP | 1702247 | B1 | 8/2015 |
| EP | 1729688 | B1 | 8/2015 |
| EP | 1887979 | B1 | 8/2015 |
| EP | 2032079 | B1 | 8/2015 |
| EP | 2219558 | B1 | 8/2015 |
| EP | 2234657 | B1 | 8/2015 |
| EP | 2250976 | B1 | 8/2015 |
| EP | 2262447 | B1 | 8/2015 |
| EP | 2303384 | B1 | 8/2015 |
| EP | 2387365 | B1 | 8/2015 |
| EP | 2560579 | B1 | 8/2015 |
| EP | 2575621 | B1 | 8/2015 |
| EP | 2590595 | B1 | 8/2015 |
| EP | 2709560 | B1 | 8/2015 |
| EP | 2755603 | B1 | 8/2015 |
| EP | 2906147 | A1 | 8/2015 |
| EP | 1534185 | B1 | 9/2015 |
| EP | 1765225 | B1 | 9/2015 |
| EP | 1778127 | B1 | 9/2015 |
| EP | 2094194 | B1 | 9/2015 |
| EP | 2201911 | B1 | 9/2015 |
| EP | 2306934 | B1 | 9/2015 |
| EP | 2397113 | B1 | 9/2015 |
| EP | 2453843 | B1 | 9/2015 |
| EP | 2459127 | B1 | 9/2015 |
| EP | 2675396 | B1 | 9/2015 |
| EP | 2675397 | B1 | 9/2015 |
| EP | 2736454 | B1 | 9/2015 |
| EP | 2754414 | A4 | 9/2015 |
| EP | 2790609 | B1 | 9/2015 |
| EP | 2805693 | B1 | 9/2015 |
| EP | 2916781 | A2 | 9/2015 |
| EP | 1734903 | B1 | 10/2015 |
| EP | 1863546 | B1 | 10/2015 |
| EP | 1900343 | B1 | 10/2015 |
| EP | 2081515 | B1 | 10/2015 |
| EP | 2191792 | B1 | 10/2015 |
| EP | 2254513 | B1 | 10/2015 |
| EP | 2381896 | B1 | 10/2015 |
| EP | 2450008 | B1 | 10/2015 |
| EP | 2544626 | B1 | 10/2015 |
| EP | 2561830 | B1 | 10/2015 |
| EP | 2600798 | B1 | 10/2015 |
| EP | 2626039 | B1 | 10/2015 |
| EP | 2647354 | B1 | 10/2015 |
| EP | 2729093 | B1 | 10/2015 |
| EP | 2836165 | B1 | 10/2015 |
| EP | 1863545 | B1 | 11/2015 |
| EP | 2303395 | B1 | 11/2015 |
| EP | 2497446 | B1 | 11/2015 |
| EP | 2772228 | B1 | 11/2015 |
| EP | 1482869 | B1 | 12/2015 |
| EP | 1551473 | B1 | 12/2015 |
| EP | 1748745 | B1 | 12/2015 |
| EP | 1755459 | B1 | 12/2015 |
| EP | 1850796 | B1 | 12/2015 |
| EP | 1922030 | B1 | 12/2015 |
| EP | 1954212 | B1 | 12/2015 |
| EP | 2424472 | B1 | 12/2015 |
| EP | 2470120 | B1 | 12/2015 |
| EP | 2542179 | B1 | 12/2015 |
| EP | 2948100 | A1 | 12/2015 |
| EP | 1991168 | B1 | 1/2016 |
| EP | 2254512 | B1 | 1/2016 |
| EP | 2422748 | B1 | 1/2016 |
| EP | 2967700 | A1 | 1/2016 |
| EP | 2967807 | A2 | 1/2016 |
| EP | 2967834 | A1 | 1/2016 |
| EP | 2967856 | A1 | 1/2016 |
| EP | 2967860 | A1 | 1/2016 |
| EP | 2967866 | A2 | 1/2016 |
| EP | 2977026 | A1 | 1/2016 |
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996641 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |

(56) References Cited

FOREIGN PATENT DOCUMENTS

| | | | |
|---|---|---|---|
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |
| EP | 2563236 | B1 | 6/2016 |
| EP | 2572675 | B1 | 6/2016 |
| EP | 2626040 | B1 | 6/2016 |
| EP | 2704668 | B1 | 6/2016 |
| EP | 2777611 | B1 | 6/2016 |
| EP | 2815724 | B1 | 6/2016 |
| EP | 2854710 | B1 | 6/2016 |
| EP | 2901966 | B1 | 6/2016 |
| EP | 3024527 | A2 | 6/2016 |
| EP | 1605866 | B1 | 7/2016 |
| EP | 1933756 | B1 | 7/2016 |
| EP | 2393452 | B1 | 7/2016 |
| EP | 2410948 | B1 | 7/2016 |
| EP | 2412397 | B1 | 7/2016 |
| EP | 2724690 | B1 | 7/2016 |
| EP | 2815723 | B1 | 7/2016 |
| EP | 2870945 | B1 | 7/2016 |
| EP | 3040054 | A1 | 7/2016 |
| EP | 3042635 | A1 | 7/2016 |
| EP | 3043745 | A1 | 7/2016 |
| EP | 3043747 | A1 | 7/2016 |
| EP | 1401358 | B1 | 8/2016 |
| EP | 1915105 | B1 | 8/2016 |
| EP | 1937186 | B1 | 8/2016 |
| EP | 2292186 | B1 | 8/2016 |
| EP | 2379012 | B1 | 8/2016 |
| EP | 2385809 | B1 | 8/2016 |
| EP | 2536345 | B1 | 8/2016 |
| EP | 2537490 | B1 | 8/2016 |
| EP | 2549954 | B1 | 8/2016 |
| EP | 2618779 | B1 | 8/2016 |
| EP | 2670352 | B1 | 8/2016 |
| EP | 2829235 | B1 | 8/2016 |
| EP | 2853238 | B1 | 8/2016 |
| EP | 2866738 | B1 | 8/2016 |
| EP | 2906150 | B1 | 8/2016 |
| EP | 3052053 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1492478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068345 | A1 | 9/2016 |
| EP | 3068346 | A1 | 9/2016 |
| EP | 3071148 | A1 | 9/2016 |
| EP | 3071149 | | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2934387 | B1 | 10/2016 |
| EP | 3076901 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2549953 | B1 | 11/2016 |
| EP | 2575696 | B1 | 11/2016 |
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3107495 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |

(56) References Cited

FOREIGN PATENT DOCUMENTS

| | | |
|---|---|---|
| EP | 3128927 A1 | 2/2017 |
| EP | 3131502 A1 | 2/2017 |
| EP | 1845895 B1 | 3/2017 |
| EP | 2190385 B1 | 3/2017 |
| EP | 2266504 B1 | 3/2017 |
| EP | 2341871 B1 | 3/2017 |
| EP | 2379011 B1 | 3/2017 |
| EP | 2379013 B1 | 3/2017 |
| EP | 2640316 B1 | 3/2017 |
| EP | 2731552 B1 | 3/2017 |
| EP | 2756109 B1 | 3/2017 |
| EP | 2773298 B1 | 3/2017 |
| EP | 2832316 B1 | 3/2017 |
| EP | 2854718 B1 | 3/2017 |
| EP | 2881083 B1 | 3/2017 |
| EP | 2934390 B1 | 3/2017 |
| EP | 2934391 B1 | 3/2017 |
| EP | 3010564 A4 | 3/2017 |
| EP | 3145451 A2 | 3/2017 |
| EP | 3146938 A1 | 3/2017 |
| EP | 2014239 B1 | 4/2017 |
| EP | 2111189 B1 | 4/2017 |
| EP | 2393451 B1 | 4/2017 |
| EP | 2617388 B1 | 4/2017 |
| EP | 2629700 B1 | 4/2017 |
| EP | 2832318 B1 | 4/2017 |
| EP | 2893904 B1 | 4/2017 |
| EP | 2982340 B1 | 4/2017 |
| EP | 3000436 B1 | 4/2017 |
| EP | 3001979 B1 | 4/2017 |
| EP | 3043749 B1 | 4/2017 |
| EP | 3045147 B1 | 4/2017 |
| EP | 3054893 B1 | 4/2017 |
| EP | 3154474 A1 | 4/2017 |
| EP | 3156007 A1 | 4/2017 |
| EP | 3157469 A1 | 4/2017 |
| EP | 1855614 B1 | 5/2017 |
| EP | 2001402 B1 | 5/2017 |
| EP | 2032080 B1 | 5/2017 |
| EP | 2262451 B1 | 5/2017 |
| EP | 2470119 B1 | 5/2017 |
| EP | 2478869 B1 | 5/2017 |
| EP | 2538880 B1 | 5/2017 |
| EP | 2545850 B1 | 5/2017 |
| EP | 2600799 B1 | 5/2017 |
| EP | 2717926 B1 | 5/2017 |
| EP | 2726024 B1 | 5/2017 |
| EP | 2805678 B1 | 5/2017 |
| EP | 2809270 B1 | 5/2017 |
| EP | 2918245 B1 | 5/2017 |
| EP | 2953579 B1 | 5/2017 |
| EP | 2976043 B1 | 5/2017 |
| EP | 2979666 B1 | 5/2017 |
| EP | 3011931 B1 | 5/2017 |
| EP | 3025682 B1 | 5/2017 |
| EP | 3033135 B1 | 5/2017 |
| EP | 3160396 | 5/2017 |
| EP | 3167847 A1 | 5/2017 |
| EP | 3169245 A1 | 5/2017 |
| EP | 3169276 A1 | 5/2017 |
| EP | 2351541 B1 | 6/2017 |
| EP | 2384165 B1 | 6/2017 |
| EP | 2400924 B1 | 6/2017 |
| EP | 2419041 B1 | 6/2017 |
| EP | 2419050 B1 | 6/2017 |
| EP | 2489331 B1 | 6/2017 |
| EP | 2493417 B1 | 6/2017 |
| EP | 2560585 B1 | 6/2017 |
| EP | 2611387 B1 | 6/2017 |
| EP | 2645967 B1 | 6/2017 |
| EP | 2677965 B1 | 6/2017 |
| EP | 2760349 B1 | 6/2017 |
| EP | 2826443 B1 | 6/2017 |
| EP | 2906148 B1 | 6/2017 |
| EP | 2929860 B1 | 6/2017 |
| EP | 2934669 B1 | 6/2017 |
| EP | 2967852 B1 | 6/2017 |
| EP | 3076901 A4 | 6/2017 |
| EP | 3174502 A1 | 6/2017 |
| EP | 3178443 A1 | 6/2017 |
| EP | 3178445 A1 | 6/2017 |
| EP | 3184081 A1 | 6/2017 |
| EP | 1624810 B1 | 7/2017 |
| EP | 2026703 B1 | 7/2017 |
| EP | 2293718 B1 | 7/2017 |
| EP | 2339989 B1 | 7/2017 |
| EP | 2344076 B1 | 7/2017 |
| EP | 2486893 B1 | 7/2017 |
| EP | 2536356 B1 | 7/2017 |
| EP | 2548534 B1 | 7/2017 |
| EP | 2608742 B1 | 7/2017 |
| EP | 2673038 B1 | 7/2017 |
| EP | 2676638 B1 | 7/2017 |
| EP | 2774630 B1 | 7/2017 |
| EP | 2825107 B1 | 7/2017 |
| EP | 2841020 B1 | 7/2017 |
| EP | 2934386 B1 | 7/2017 |
| EP | 2943151 B1 | 7/2017 |
| EP | 3058894 B1 | 7/2017 |
| EP | 3071151 B1 | 7/2017 |
| EP | 3191025 A1 | 7/2017 |
| EP | 3193740 A2 | 7/2017 |
| EP | 3193782 A1 | 7/2017 |
| EP | 1530441 B1 | 8/2017 |
| EP | 1722716 B1 | 8/2017 |
| EP | 1971289 B1 | 8/2017 |
| EP | 2323591 B1 | 8/2017 |
| EP | 2344070 B1 | 8/2017 |
| EP | 2393442 A4 | 8/2017 |
| EP | 2413842 B1 | 8/2017 |
| EP | 2427143 B1 | 8/2017 |
| EP | 2459077 B1 | 8/2017 |
| EP | 2480167 B1 | 8/2017 |
| EP | 2482749 B1 | 8/2017 |
| EP | 2496181 B1 | 8/2017 |
| EP | 2568925 B1 | 8/2017 |
| EP | 2617389 B1 | 8/2017 |
| EP | 2713954 B1 | 8/2017 |
| EP | 2755602 B1 | 8/2017 |
| EP | 2800602 B1 | 8/2017 |
| EP | 2809263 B1 | 8/2017 |
| EP | 2830536 B1 | 8/2017 |
| EP | 2841009 B1 | 8/2017 |
| EP | 2844190 B1 | 8/2017 |
| EP | 2849681 B1 | 8/2017 |
| EP | 2858600 B1 | 8/2017 |
| EP | 2897556 B1 | 8/2017 |
| EP | 2934388 B1 | 8/2017 |
| EP | 2979667 B1 | 8/2017 |
| EP | 3197397 A1 | 8/2017 |
| EP | 3202371 A1 | 8/2017 |
| EP | 3206629 B1 | 8/2017 |
| EP | 3206631 A2 | 8/2017 |
| EP | 1799093 B1 | 9/2017 |
| EP | 2010103 B1 | 9/2017 |
| EP | 2114304 B1 | 9/2017 |
| EP | 2344090 B1 | 9/2017 |
| EP | 2398421 B1 | 9/2017 |
| EP | 2437687 B1 | 9/2017 |
| EP | 2453970 B1 | 9/2017 |
| EP | 2509538 B1 | 9/2017 |
| EP | 2713956 B1 | 9/2017 |
| EP | 2772227 B1 | 9/2017 |
| EP | 2787924 B1 | 9/2017 |
| EP | 2803335 B1 | 9/2017 |
| EP | 2811939 B1 | 9/2017 |
| EP | 2830537 B1 | 9/2017 |
| EP | 2865355 B1 | 9/2017 |
| EP | 2872047 B1 | 9/2017 |
| EP | 2934389 B1 | 9/2017 |
| EP | 3213715 A1 | 9/2017 |
| EP | 3213716 A1 | 9/2017 |
| EP | 3215061 A1 | 9/2017 |
| EP | 3220856 A2 | 9/2017 |

(56) References Cited

FOREIGN PATENT DOCUMENTS

| | | |
|---|---|---|
| EP | 3220857 | 9/2017 |
| EP | 1945141 B1 | 10/2017 |
| EP | 2317956 B1 | 10/2017 |
| EP | 2613737 B1 | 10/2017 |
| EP | 2620125 B1 | 10/2017 |
| EP | 2720642 B1 | 10/2017 |
| EP | 2741682 B1 | 10/2017 |
| EP | 2872077 B1 | 10/2017 |
| EP | 3021925 B1 | 10/2017 |
| EP | 3232989 A1 | 10/2017 |
| EP | 1651148 B1 | 11/2017 |
| EP | 1913901 B1 | 11/2017 |
| EP | 2222248 B1 | 11/2017 |
| EP | 2296581 B1 | 11/2017 |
| EP | 2326264 B1 | 11/2017 |
| EP | 2427142 B1 | 11/2017 |
| EP | 2456483 B1 | 11/2017 |
| EP | 2493423 B1 | 11/2017 |
| EP | 2611391 B1 | 11/2017 |
| EP | 2618780 B1 | 11/2017 |
| EP | 2658480 B1 | 11/2017 |
| EP | 2710978 B1 | 11/2017 |
| EP | 2832315 B1 | 11/2017 |
| EP | 2954875 B1 | 11/2017 |
| EP | 2967861 B1 | 11/2017 |
| EP | 2982338 B1 | 11/2017 |
| EP | 3027144 B1 | 11/2017 |
| EP | 3043746 B1 | 11/2017 |
| EP | 3049026 B1 | 11/2017 |
| EP | 3068311 B1 | 11/2017 |
| EP | 3110368 B1 | 11/2017 |
| EP | 3110369 B1 | 11/2017 |
| EP | 3132773 B1 | 11/2017 |
| EP | 3238662 A1 | 11/2017 |
| EP | 3245980 | 11/2017 |
| EP | 3247312 A1 | 11/2017 |
| EP | 1667603 B1 | 12/2017 |
| EP | 1874954 B1 | 12/2017 |
| EP | 2427145 B1 | 12/2017 |
| EP | 2542185 B1 | 12/2017 |
| EP | 2670351 | 12/2017 |
| EP | 2723274 B1 | 12/2017 |
| EP | 2736455 B1 | 12/2017 |
| EP | 2736457 B1 | 12/2017 |
| EP | 2830534 B1 | 12/2017 |
| EP | 2830535 B1 | 12/2017 |
| EP | 2911592 B1 | 12/2017 |
| EP | 2916772 B1 | 12/2017 |
| EP | 2967922 B1 | 12/2017 |
| EP | 3009105 B1 | 12/2017 |
| EP | 3088037 B1 | 12/2017 |
| EP | 3115023 B1 | 12/2017 |
| EP | 3251633 A1 | 12/2017 |
| EP | 3253332 A2 | 12/2017 |
| EP | 3256073 A1 | 12/2017 |
| EP | 3256074 A1 | 12/2017 |
| EP | 3256076 A1 | 12/2017 |
| EP | 3256178 A1 | 12/2017 |
| EP | 1492458 B1 | 1/2018 |
| EP | 1768604 B1 | 1/2018 |
| EP | 1951154 B1 | 1/2018 |
| EP | 2091465 B1 | 1/2018 |
| EP | 2345380 B1 | 1/2018 |
| EP | 2456363 B1 | 1/2018 |
| EP | 2531143 B1 | 1/2018 |
| EP | 2621407 B1 | 1/2018 |
| EP | 2694123 B1 | 1/2018 |
| EP | 2775962 B1 | 1/2018 |
| EP | 2874568 B1 | 1/2018 |
| EP | 2967863 B1 | 1/2018 |
| EP | 2967869 B1 | 1/2018 |
| EP | 3033047 B1 | 1/2018 |
| EP | 3037065 B1 | 1/2018 |
| EP | 3049025 B1 | 1/2018 |
| EP | 3052052 B1 | 1/2018 |
| EP | 3078350 B1 | 1/2018 |
| EP | 3267946 A1 | 1/2018 |
| EP | 3269331 A1 | 1/2018 |
| EP | 3273911 A1 | 1/2018 |
| EP | 3275404 A1 | 1/2018 |
| EP | 2197512 B1 | 2/2018 |
| EP | 2248486 B1 | 2/2018 |
| EP | 2344066 B1 | 2/2018 |
| EP | 2381854 B1 | 2/2018 |
| EP | 2667823 B1 | 2/2018 |
| EP | 2699169 B1 | 2/2018 |
| EP | 2714177 B1 | 2/2018 |
| EP | 2736544 B1 | 2/2018 |
| EP | 2846736 B1 | 2/2018 |
| EP | 2886082 B1 | 2/2018 |
| EP | 2886084 B1 | 2/2018 |
| EP | 2931178 B1 | 2/2018 |
| EP | 2934392 B1 | 2/2018 |
| EP | 3150173 B1 | 2/2018 |
| EP | 3277222 A1 | 2/2018 |
| EP | 3281608 A1 | 2/2018 |
| EP | 3283009 A1 | 2/2018 |
| EP | 3283011 A1 | 2/2018 |
| EP | 3287099 A1 | 2/2018 |
| EP | 1959864 B1 | 3/2018 |
| EP | 2513200 B1 | 3/2018 |
| EP | 2608815 B1 | 3/2018 |
| EP | 2858711 B1 | 3/2018 |
| EP | 2938292 B1 | 3/2018 |
| EP | 2943132 B1 | 3/2018 |
| EP | 2983620 B1 | 3/2018 |
| EP | 3003219 B1 | 3/2018 |
| EP | 3005979 B1 | 3/2018 |
| EP | 3037064 B1 | 3/2018 |
| EP | 3046511 B1 | 3/2018 |
| EP | 3142603 B1 | 3/2018 |
| EP | 3288479 A1 | 3/2018 |
| EP | 3288494 A1 | 3/2018 |
| EP | 3288497 A2 | 3/2018 |
| EP | 3288498 A1 | 3/2018 |
| EP | 3288499 A1 | 3/2018 |
| EP | 3290004 A1 | 3/2018 |
| EP | 3290007 A1 | 3/2018 |
| EP | 3294214 A1 | 3/2018 |
| EP | 3294215 A1 | 3/2018 |
| EP | 3294218 A1 | 3/2018 |
| EP | 3298970 A1 | 3/2018 |
| EP | 3298987 A1 | 3/2018 |
| EP | 3298988 | 3/2018 |
| EP | 2209440 B1 | 4/2018 |
| EP | 2536357 B1 | 4/2018 |
| EP | 2605725 B1 | 4/2018 |
| EP | 2608743 B1 | 4/2018 |
| EP | 2709561 B1 | 4/2018 |
| EP | 2787925 B1 | 4/2018 |
| EP | 2789314 B1 | 4/2018 |
| EP | 2900150 B1 | 4/2018 |
| EP | 2908779 B1 | 4/2018 |
| EP | 2922502 B1 | 4/2018 |
| EP | 2964441 B1 | 4/2018 |
| EP | 2967868 B1 | 4/2018 |
| EP | 2979665 B1 | 4/2018 |
| EP | 2994073 B1 | 4/2018 |
| EP | 3095394 B1 | 4/2018 |
| EP | 3128927 A4 | 4/2018 |
| EP | 3134033 B1 | 4/2018 |
| EP | 3137146 A4 | 4/2018 |
| EP | 3280482 A4 | 4/2018 |
| EP | 3302297 A2 | 4/2018 |
| EP | 3302362 A1 | 4/2018 |
| EP | 3310301 A1 | 4/2018 |
| EP | 3311774 A1 | 4/2018 |
| EP | 3311783 A1 | 4/2018 |
| EP | 1945112 B1 | 5/2018 |
| EP | 2007313 B1 | 5/2018 |
| EP | 2316381 B2 | 5/2018 |
| EP | 2377469 B1 | 5/2018 |
| EP | 2531115 B1 | 5/2018 |
| EP | 2561831 B1 | 5/2018 |

(56) References Cited

FOREIGN PATENT DOCUMENTS

| | | | |
|---|---|---|---|
| EP | 2605724 | B1 | 5/2018 |
| EP | 2723277 | B1 | 5/2018 |
| EP | 2741711 | B1 | 5/2018 |
| EP | 2755573 | B1 | 5/2018 |
| EP | 2768429 | B1 | 5/2018 |
| EP | 2819618 | B1 | 5/2018 |
| EP | 2833836 | B1 | 5/2018 |
| EP | 2886083 | B1 | 5/2018 |
| EP | 2926840 | B1 | 5/2018 |
| EP | 2943157 | B1 | 5/2018 |
| EP | 2948099 | B1 | 5/2018 |
| EP | 3000437 | B1 | 5/2018 |
| EP | 3145448 | B1 | 5/2018 |
| EP | 3154475 | B1 | 5/2018 |
| EP | 3316819 | A1 | 5/2018 |
| EP | 3316821 | A1 | 5/2018 |
| EP | 3322381 | A1 | 5/2018 |
| EP | 3323353 | A1 | 5/2018 |
| EP | 3323439 | A1 | 5/2018 |
| EP | 3324892 | A1 | 5/2018 |
| EP | 3326584 | A1 | 5/2018 |
| EP | 2150312 | B1 | 6/2018 |
| EP | 2379322 | B1 | 6/2018 |
| EP | 2400925 | B1 | 6/2018 |
| EP | 2552355 | B1 | 6/2018 |
| EP | 2560589 | B1 | 6/2018 |
| EP | 2563277 | B1 | 6/2018 |
| EP | 2661305 | B1 | 6/2018 |
| EP | 2736456 | B1 | 6/2018 |
| EP | 2782523 | B1 | 6/2018 |
| EP | 3056170 | B1 | 6/2018 |
| EP | 3062745 | B1 | 6/2018 |
| EP | 3130320 | B1 | 6/2018 |
| EP | 3187150 | B1 | 6/2018 |
| EP | 3334380 | A1 | 6/2018 |
| EP | 3334381 | A1 | 6/2018 |
| EP | 3335670 | A1 | 6/2018 |
| EP | 3337412 | A1 | 6/2018 |
| EP | 3337424 | A1 | 6/2018 |
| EP | 2478872 | B1 | 7/2018 |
| EP | 2563278 | B1 | 7/2018 |
| EP | 2616004 | B1 | 7/2018 |
| EP | 2779943 | B1 | 7/2018 |
| EP | 2802290 | B1 | 7/2018 |
| EP | 2816980 | B1 | 7/2018 |
| EP | 2938293 | B1 | 7/2018 |
| EP | 3107496 | B1 | 7/2018 |
| EP | 3178450 | B1 | 7/2018 |
| EP | 3212097 | B1 | 7/2018 |
| EP | 3340936 | A1 | 7/2018 |
| EP | 3342355 | A1 | 7/2018 |
| EP | 3342377 | A1 | 7/2018 |
| EP | 3347182 | | 7/2018 |
| EP | 3348235 | A1 | 7/2018 |
| EP | 3349693 | A1 | 7/2018 |
| EP | 2536354 | B1 | 8/2018 |
| EP | 2616006 | B1 | 8/2018 |
| EP | 2797556 | B1 | 8/2018 |
| EP | 2822473 | B1 | 8/2018 |
| EP | 2854711 | B1 | 8/2018 |
| EP | 2866847 | B1 | 8/2018 |
| EP | 2918246 | B1 | 8/2018 |
| EP | 2967845 | B1 | 8/2018 |
| EP | 2999436 | B1 | 8/2018 |
| EP | 3013281 | B1 | 8/2018 |
| EP | 3060170 | B1 | 8/2018 |
| EP | 3104811 | B1 | 8/2018 |
| EP | 3143944 | B1 | 8/2018 |
| EP | 3157467 | B1 | 8/2018 |
| EP | 3193791 | B1 | 8/2018 |
| EP | 3241526 | B1 | 8/2018 |
| EP | 3355800 | A1 | 8/2018 |
| EP | 3360513 | A1 | 8/2018 |
| EP | 3360514 | A1 | 8/2018 |
| EP | 3361988 | A1 | 8/2018 |
| EP | 2114305 | B1 | 9/2018 |
| EP | 2155115 | B1 | 9/2018 |
| EP | 2601910 | B1 | 9/2018 |
| EP | 2617390 | B1 | 9/2018 |
| EP | 2734157 | B1 | 9/2018 |
| EP | 2968674 | B1 | 9/2018 |
| EP | 2999415 | B1 | 9/2018 |
| EP | 3106130 | B1 | 9/2018 |
| EP | 3151763 | B1 | 9/2018 |
| EP | 3213717 | B1 | 9/2018 |
| EP | 3245985 | B1 | 9/2018 |
| EP | 3367979 | A1 | 9/2018 |
| EP | 1827256 | B1 | 10/2018 |
| EP | 1850790 | B1 | 10/2018 |
| EP | 2063823 | B1 | 10/2018 |
| EP | 2124825 | B1 | 10/2018 |
| EP | 2249746 | B1 | 10/2018 |
| EP | 2254514 | B1 | 10/2018 |
| EP | 2285309 | B1 | 10/2018 |
| EP | 2455042 | B1 | 10/2018 |
| EP | 2571561 | B1 | 10/2018 |
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2836171 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |
| EP | 3120809 | B1 | 10/2018 |
| EP | 3238663 | B1 | 10/2018 |
| EP | 3275404 | A4 | 10/2018 |
| EP | 3384879 | A1 | 10/2018 |
| EP | 3389557 | | 10/2018 |
| EP | 1708650 | B1 | 11/2018 |
| EP | 1945143 | B1 | 11/2018 |
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3145452 | B1 | 11/2018 |
| EP | 3216424 | B1 | 11/2018 |
| EP | 3260084 | B1 | 11/2018 |
| EP | 3397206 | A1 | 11/2018 |
| EP | 3400908 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |

(56) References Cited

FOREIGN PATENT DOCUMENTS

| | | |
|---|---|---|
| EP | 3266416 B1 | 12/2018 |
| EP | 3326583 B1 | 12/2018 |
| EP | 3410987 A1 | 12/2018 |
| EP | 3417813 A1 | 12/2018 |
| EP | 2129332 B1 | 1/2019 |
| EP | 2196159 B1 | 1/2019 |
| EP | 2370025 B1 | 1/2019 |
| EP | 2549957 B1 | 1/2019 |
| EP | 2819619 B1 | 1/2019 |
| EP | 2849680 B1 | 1/2019 |
| EP | 2856972 B1 | 1/2019 |
| EP | 2866742 B1 | 1/2019 |
| EP | 2884946 B1 | 1/2019 |
| EP | 2948102 B1 | 1/2019 |
| EP | 2979664 B1 | 1/2019 |
| EP | 3043748 B1 | 1/2019 |
| EP | 3145449 B1 | 1/2019 |
| EP | 3332743 B1 | 1/2019 |
| EP | 3429507 A1 | 1/2019 |
| EP | 3432832 A1 | 1/2019 |
| EP | 3432834 A1 | 1/2019 |
| EP | 1895943 B1 | 2/2019 |
| EP | 2070490 B1 | 2/2019 |
| EP | 2308425 B1 | 2/2019 |
| EP | 2379009 B1 | 2/2019 |
| EP | 2575685 B1 | 2/2019 |
| EP | 2688562 B1 | 2/2019 |
| EP | 2714068 B1 | 2/2019 |
| EP | 2720641 B1 | 2/2019 |
| EP | 2760375 B1 | 2/2019 |
| EP | 2862590 B1 | 2/2019 |
| EP | 2925259 B1 | 2/2019 |
| EP | 2931179 B1 | 2/2019 |
| EP | 3005983 B1 | 2/2019 |
| EP | 3023117 B1 | 2/2019 |
| EP | 3184083 B1 | 2/2019 |
| EP | 3202333 B1 | 2/2019 |
| EP | 3261583 B1 | 2/2019 |
| EP | 3278832 B1 | 2/2019 |
| EP | 3435919 A1 | 2/2019 |
| EP | 3441045 A1 | 2/2019 |
| EP | 3442469 A1 | 2/2019 |
| EP | 3445290 A1 | 2/2019 |
| EP | 1771132 B1 | 3/2019 |
| EP | 1959866 B1 | 3/2019 |
| EP | 2120794 B1 | 3/2019 |
| EP | 2259728 B1 | 3/2019 |
| EP | 2344074 B1 | 3/2019 |
| EP | 2552356 B1 | 3/2019 |
| EP | 2598044 B1 | 3/2019 |
| EP | 2659861 B1 | 3/2019 |
| EP | 2670357 B1 | 3/2019 |
| EP | 2898902 B1 | 3/2019 |
| EP | 2948098 B1 | 3/2019 |
| EP | 2948101 B1 | 3/2019 |
| EP | 2967865 B1 | 3/2019 |
| EP | 2974695 B1 | 3/2019 |
| EP | 3027243 B1 | 3/2019 |
| EP | 3116446 B1 | 3/2019 |
| EP | 3145445 B1 | 3/2019 |
| EP | 3151783 B1 | 3/2019 |
| EP | 3151784 B1 | 3/2019 |
| EP | 3278768 B1 | 3/2019 |
| EP | 3320943 B1 | 3/2019 |
| EP | 3454785 A1 | 3/2019 |
| EP | 3454786 A1 | 3/2019 |
| EP | 3454794 A1 | 3/2019 |
| EP | 3457987 A1 | 3/2019 |
| EP | 3457988 A1 | 3/2019 |
| EP | 1793745 B1 | 4/2019 |
| EP | 1855623 B1 | 4/2019 |
| EP | 2129333 B1 | 4/2019 |
| EP | 2149349 B1 | 4/2019 |
| EP | 2438888 B1 | 4/2019 |
| EP | 2484309 B1 | 4/2019 |
| EP | 2519268 B1 | 4/2019 |
| EP | 2528545 B1 | 4/2019 |
| EP | 2536358 B1 | 4/2019 |
| EP | 2661239 B1 | 4/2019 |
| EP | 2709563 B1 | 4/2019 |
| EP | 2736451 B1 | 4/2019 |
| EP | 2810619 B1 | 4/2019 |
| EP | 2810622 B1 | 4/2019 |
| EP | 2879589 B1 | 4/2019 |
| EP | 2921198 B1 | 4/2019 |
| EP | 2986256 B1 | 4/2019 |
| EP | 3090704 B1 | 4/2019 |
| EP | 3116445 B1 | 4/2019 |
| EP | 3141217 B1 | 4/2019 |
| EP | 3193745 B1 | 4/2019 |
| EP | 3241525 B1 | 4/2019 |
| EP | 3344167 A4 | 4/2019 |
| EP | 3461531 A1 | 4/2019 |
| EP | 3463120 | 4/2019 |
| EP | 1703870 B1 | 5/2019 |
| EP | 1708642 B1 | 5/2019 |
| EP | 2240121 B1 | 5/2019 |
| EP | 2663259 B1 | 5/2019 |
| EP | 2695586 B1 | 5/2019 |
| EP | 2726018 B1 | 5/2019 |
| EP | 2954872 B1 | 5/2019 |
| EP | 3110370 B1 | 5/2019 |
| EP | 3111890 B1 | 5/2019 |
| EP | 3182932 B1 | 5/2019 |
| EP | 3192472 B1 | 5/2019 |
| EP | 3238661 B1 | 5/2019 |
| EP | 3284503 B1 | 5/2019 |
| EP | 3302364 B1 | 5/2019 |
| EP | 3315094 B1 | 5/2019 |
| EP | 3316818 B1 | 5/2019 |
| EP | 3474778 A1 | 5/2019 |
| EP | 3476366 A1 | 5/2019 |
| EP | 3476424 A1 | 5/2019 |
| EP | 3479797 A1 | 5/2019 |
| EP | 3481336 A1 | 5/2019 |
| EP | 3481338 A1 | 5/2019 |
| EP | 3481339 A1 | 5/2019 |
| EP | 3482718 A1 | 5/2019 |
| EP | 3484412 A1 | 5/2019 |
| EP | 3485847 A1 | 5/2019 |
| EP | 3485848 A1 | 5/2019 |
| EP | 3485933 A1 | 5/2019 |
| EP | 3487420 A1 | 5/2019 |
| EP | 3487451 A1 | 5/2019 |
| EP | 3488822 A1 | 5/2019 |
| EP | 307115081 | 5/2019 |
| EP | 1624792 B1 | 6/2019 |
| EP | 1737394 B1 | 6/2019 |
| EP | 1858451 B1 | 6/2019 |
| EP | 1895944 B1 | 6/2019 |
| EP | 1968487 B1 | 6/2019 |
| EP | 2004095 B1 | 6/2019 |
| EP | 2010102 B1 | 6/2019 |
| EP | 2131788 B1 | 6/2019 |
| EP | 2560580 B1 | 6/2019 |
| EP | 2618782 B1 | 6/2019 |
| EP | 2868296 B1 | 6/2019 |
| EP | 2961358 B1 | 6/2019 |
| EP | 2967847 B1 | 6/2019 |
| EP | 2985006 B1 | 6/2019 |
| EP | 3033048 B1 | 6/2019 |
| EP | 3119451 B1 | 6/2019 |
| EP | 3131503 B1 | 6/2019 |
| EP | 3213718 B1 | 6/2019 |
| EP | 3275390 B1 | 6/2019 |
| EP | 3300692 B1 | 6/2019 |
| EP | 3326585 B1 | 6/2019 |
| EP | 3338737 B1 | 6/2019 |
| EP | 3357457 B1 | 6/2019 |
| EP | 3372198 B1 | 6/2019 |
| EP | 3490465 A1 | 6/2019 |
| EP | 3496626 A1 | 6/2019 |
| EP | 3496664 A1 | 6/2019 |
| EP | 3498224 A1 | 6/2019 |

(56) References Cited

FOREIGN PATENT DOCUMENTS

| | | |
|---|---|---|
| EP | 3501454 A1 | 6/2019 |
| EP | 1659981 B1 | 7/2019 |
| EP | 1924223 B1 | 7/2019 |
| EP | 2249745 B1 | 7/2019 |
| EP | 2296744 B1 | 7/2019 |
| EP | 2331019 B1 | 7/2019 |
| EP | 2368527 B1 | 7/2019 |
| EP | 2509542 B1 | 7/2019 |
| EP | 2555710 B1 | 7/2019 |
| EP | 2575682 B1 | 7/2019 |
| EP | 2575683 B1 | 7/2019 |
| EP | 2640431 B1 | 7/2019 |
| EP | 2641572 B1 | 7/2019 |
| EP | 2649964 B1 | 7/2019 |
| EP | 2767260 B1 | 7/2019 |
| EP | 2777615 B1 | 7/2019 |
| EP | 2838476 B1 | 7/2019 |
| EP | 2861186 B1 | 7/2019 |
| EP | 2877124 B1 | 7/2019 |
| EP | 2877132 B1 | 7/2019 |
| EP | 2921565 B1 | 7/2019 |
| EP | 2938291 B1 | 7/2019 |
| EP | 2999433 B1 | 7/2019 |
| EP | 3145450 B1 | 7/2019 |
| EP | 3254644 B1 | 7/2019 |
| EP | 3315093 B1 | 7/2019 |
| EP | 3344189 B1 | 7/2019 |
| EP | 3503813 A1 | 7/2019 |
| EP | 3503846 A1 | 7/2019 |
| EP | 3503847 A1 | 7/2019 |
| EP | 3503848 A1 | 7/2019 |
| EP | 3505077 A1 | 7/2019 |
| EP | 3512465 A1 | 7/2019 |
| EP | 1861043 B1 | 8/2019 |
| EP | 2303190 B1 | 8/2019 |
| EP | 2593171 B1 | 8/2019 |
| EP | 2632393 B1 | 8/2019 |
| EP | 2663355 B1 | 8/2019 |
| EP | 2665509 B1 | 8/2019 |
| EP | 2688525 B1 | 8/2019 |
| EP | 2699201 B1 | 8/2019 |
| EP | 2755564 B1 | 8/2019 |
| EP | 2769681 B1 | 8/2019 |
| EP | 2793751 B1 | 8/2019 |
| EP | 2900177 B1 | 8/2019 |
| EP | 2967536 B1 | 8/2019 |
| EP | 3050541 B1 | 8/2019 |
| EP | 3102152 B1 | 8/2019 |
| EP | 3157607 B1 | 8/2019 |
| EP | 3231392 B1 | 8/2019 |
| EP | 3284411 B1 | 8/2019 |
| EP | 3328318 B1 | 8/2019 |
| EP | 3348233 B1 | 8/2019 |
| EP | 3366262 B1 | 8/2019 |
| EP | 3527170 A1 | 8/2019 |
| EP | 3530236 A1 | 8/2019 |
| EP | 2358297 B1 | 9/2019 |
| EP | 2368525 B1 | 9/2019 |
| EP | 2542186 B1 | 9/2019 |
| EP | 2656863 B1 | 9/2019 |
| EP | 3003221 B1 | 9/2019 |
| EP | 3003452 B1 | 9/2019 |
| EP | 3220971 B1 | 9/2019 |
| EP | 3223874 B1 | 9/2019 |
| EP | 3288495 B1 | 9/2019 |
| EP | 3311776 B1 | 9/2019 |
| EP | 3334379 B1 | 9/2019 |
| EP | 3531975 A1 | 9/2019 |
| EP | 3534840 A1 | 9/2019 |
| EP | 3534845 A2 | 9/2019 |
| EP | 3535010 A1 | 9/2019 |
| EP | 3538027 A1 | 9/2019 |
| EP | 3539508 A1 | 9/2019 |
| EP | 3539509 A1 | 9/2019 |
| EP | 1740265 B1 | 10/2019 |
| EP | 2039756 B1 | 10/2019 |
| EP | 2456506 B1 | 10/2019 |
| EP | 2470122 B1 | 10/2019 |
| EP | 2613738 B1 | 10/2019 |
| EP | 2637607 B1 | 10/2019 |
| EP | 2674174 B1 | 10/2019 |
| EP | 2811923 B1 | 10/2019 |
| EP | 2901967 B1 | 10/2019 |
| EP | 3010431 B1 | 10/2019 |
| EP | 3019091 B1 | 10/2019 |
| EP | 3019123 B1 | 10/2019 |
| EP | 3057522 B1 | 10/2019 |
| EP | 3067075 B1 | 10/2019 |
| EP | 3146937 B1 | 10/2019 |
| EP | 3238777 B1 | 10/2019 |
| EP | 3359211 B1 | 10/2019 |
| EP | 3388026 B1 | 10/2019 |
| EP | 3432806 B1 | 10/2019 |
| EP | 3496626 A4 | 10/2019 |
| EP | 3544548 A1 | 10/2019 |
| EP | 3547936 A1 | 10/2019 |
| EP | 3547966 A1 | 10/2019 |
| EP | 3549555 A1 | 10/2019 |
| EP | 3554424 | 10/2019 |
| EP | 3558165 A1 | 10/2019 |
| EP | 3558168 A1 | 10/2019 |
| EP | 3558169 A2 | 10/2019 |
| EP | 2043559 B1 | 11/2019 |
| EP | 2358308 B1 | 11/2019 |
| EP | 2405863 B1 | 11/2019 |
| EP | 2701633 B1 | 11/2019 |
| EP | 2898857 B1 | 11/2019 |
| EP | 2967853 B1 | 11/2019 |
| EP | 3009104 B1 | 11/2019 |
| EP | 3021792 B1 | 11/2019 |
| EP | 3076900 B1 | 11/2019 |
| EP | 3111889 B1 | 11/2019 |
| EP | 3142607 B1 | 11/2019 |
| EP | 3167850 B1 | 11/2019 |
| EP | 3397205 B1 | 11/2019 |
| EP | 3572117 A1 | 11/2019 |
| EP | 3479800 A4 | 12/2019 |
| EP | 3576677 A1 | 12/2019 |
| EP | 3579761 A2 | 12/2019 |
| EP | 3579788 | 12/2019 |
| EP | 3582697 A1 | 12/2019 |
| EP | 3583922 A1 | 12/2019 |
| EP | 3445443 A4 | 1/2020 |
| EP | 3590471 A1 | 1/2020 |
| EP | 3590472 A1 | 1/2020 |
| EP | 3592284 A1 | 1/2020 |
| EP | 3592288 A1 | 1/2020 |
| EP | 3592289 A1 | 1/2020 |
| EP | 3593763 A1 | 1/2020 |
| EP | 3600159 A1 | 2/2020 |
| EP | 3606472 A1 | 2/2020 |
| EP | 2241287 B2 | 3/2020 |
| EP | 2376013 B1 | 3/2020 |
| EP | 2911593 B1 | 3/2020 |
| EP | 2995279 B1 | 3/2020 |
| EP | 3009103 B1 | 3/2020 |
| EP | 3038664 B1 | 3/2020 |
| EP | 3175822 B1 | 3/2020 |
| EP | 3179960 B1 | 3/2020 |
| EP | 3280479 B1 | 3/2020 |
| EP | 3616651 A1 | 3/2020 |
| EP | 3619136 A1 | 3/2020 |
| EP | 3626208 A1 | 3/2020 |
| EP | 1667614 B2 | 4/2020 |
| EP | 2119417 B2 | 4/2020 |
| EP | 2155114 B1 | 4/2020 |
| EP | 2299937 B1 | 4/2020 |
| EP | 2331016 B1 | 4/2020 |
| EP | 2376013 B8 | 4/2020 |
| EP | 2413843 B1 | 4/2020 |
| EP | 2854705 B1 | 4/2020 |
| EP | 2918249 B1 | 4/2020 |
| EP | 2922593 B1 | 4/2020 |
| EP | 2950753 B1 | 4/2020 |

(56) References Cited

FOREIGN PATENT DOCUMENTS

| | | | |
|---|---|---|---|
| EP | 2967810 B1 | 4/2020 |
| EP | 3110367 B1 | 4/2020 |
| EP | 3111888 B1 | 4/2020 |
| EP | 3128927 B1 | 4/2020 |
| EP | 3134032 B1 | 4/2020 |
| EP | 3142606 B1 | 4/2020 |
| EP | 3270825 B1 | 4/2020 |
| EP | 3300696 B1 | 4/2020 |
| EP | 3316823 B1 | 4/2020 |
| EP | 3334487 B1 | 4/2020 |
| EP | 3342355 B1 | 4/2020 |
| EP | 3373863 B1 | 4/2020 |
| EP | 3459498 B1 | 4/2020 |
| EP | 3470105 B1 | 4/2020 |
| EP | 3628239 A1 | 4/2020 |
| EP | 3628274 | 4/2020 |
| EP | 3632338 A1 | 4/2020 |
| EP | 3636312 A1 | 4/2020 |
| EP | 3639792 A1 | 4/2020 |
| EP | 3639888 A1 | 4/2020 |
| EP | 3643273 A1 | 4/2020 |
| EP | 1895942 B1 | 5/2020 |
| EP | 2120821 B1 | 5/2020 |
| EP | 2437688 B1 | 5/2020 |
| EP | 2785281 B1 | 5/2020 |
| EP | 2852354 B1 | 5/2020 |
| EP | 2884906 B1 | 5/2020 |
| EP | 2999412 B1 | 5/2020 |
| EP | 3060174 B1 | 5/2020 |
| EP | 3071147 B1 | 5/2020 |
| EP | 3104812 B1 | 5/2020 |
| EP | 3139861 B1 | 5/2020 |
| EP | 3232989 B1 | 5/2020 |
| EP | 3294219 B1 | 5/2020 |
| EP | 3298970 B1 | 5/2020 |
| EP | 3302366 B1 | 5/2020 |
| EP | 3323389 B1 | 5/2020 |
| EP | 3332744 B1 | 5/2020 |
| EP | 3402440 B1 | 5/2020 |
| EP | 3417813 B1 | 5/2020 |
| EP | 3417831 B1 | 5/2020 |
| EP | 3457987 B1 | 5/2020 |
| EP | 3484413 B1 | 5/2020 |
| EP | 3531975 B1 | 5/2020 |
| EP | 3644866 A1 | 5/2020 |
| EP | 3646822 A1 | 5/2020 |
| EP | 3646824 A1 | 5/2020 |
| EP | 3646825 A1 | 5/2020 |
| EP | 3656354 A1 | 5/2020 |
| EP | 1648339 B2 | 6/2020 |
| EP | 2072027 B1 | 6/2020 |
| EP | 2331016 B8 | 6/2020 |
| EP | 2616007 B1 | 6/2020 |
| EP | 2967856 B1 | 6/2020 |
| EP | 3042635 B1 | 6/2020 |
| EP | 3060165 B1 | 6/2020 |
| EP | 3280338 B1 | 6/2020 |
| EP | 3283010 B1 | 6/2020 |
| EP | 3400908 B1 | 6/2020 |
| EP | 3494928 B1 | 6/2020 |
| EP | 3498225 B1 | 6/2020 |
| EP | 3583920 B1 | 6/2020 |
| EP | 3659553 A1 | 6/2020 |
| EP | 3668450 A1 | 6/2020 |
| EP | 3668452 A1 | 6/2020 |
| EP | 3669828 A1 | 6/2020 |
| EP | 3669829 A1 | 6/2020 |
| EP | 2271284 B1 | 7/2020 |
| EP | 2291145 B1 | 7/2020 |
| EP | 2512952 B1 | 7/2020 |
| EP | 2558029 B1 | 7/2020 |
| EP | 2693985 B1 | 7/2020 |
| EP | 2858708 B1 | 7/2020 |
| EP | 2862546 B1 | 7/2020 |
| EP | 2967807 B1 | 7/2020 |
| EP | 2967866 B1 | 7/2020 |
| EP | 3061421 B1 | 7/2020 |
| EP | 3107497 B1 | 7/2020 |
| EP | 3423000 B1 | 7/2020 |
| EP | 3441045 B1 | 7/2020 |
| EP | 3451972 B1 | 7/2020 |
| EP | 3501454 B1 | 7/2020 |
| EP | 3512466 B1 | 7/2020 |
| EP | 3616652 B1 | 7/2020 |
| EP | 3672528 A1 | 7/2020 |
| EP | 3672529 A1 | 7/2020 |
| EP | 3672532 | 7/2020 |
| EP | 3673925 A1 | 7/2020 |
| EP | 3679894 A1 | 7/2020 |
| EP | 3681439 A1 | 7/2020 |
| EP | 3681441 A1 | 7/2020 |
| EP | 3682852 A1 | 7/2020 |
| EP | 3682854 A1 | 7/2020 |
| EP | 2367505 B1 | 8/2020 |
| EP | 2497445 B1 | 8/2020 |
| EP | 2537486 B1 | 8/2020 |
| EP | 2777616 B1 | 8/2020 |
| EP | 3007651 B1 | 8/2020 |
| EP | 3052053 B1 | 8/2020 |
| EP | 3237033 B1 | 8/2020 |
| EP | 3388005 B1 | 8/2020 |
| EP | 3410986 B1 | 8/2020 |
| EP | 3451974 B1 | 8/2020 |
| EP | 3463192 B1 | 8/2020 |
| EP | 3554423 B1 | 8/2020 |
| EP | 3568089 A4 | 8/2020 |
| EP | 3573544 B1 | 8/2020 |
| EP | 3634255 B1 | 8/2020 |
| EP | 3689299 A1 | 8/2020 |
| EP | 3691567 A1 | 8/2020 |
| EP | 3697342 | 8/2020 |
| EP | 3697346 A1 | 8/2020 |
| EP | 2485795 B1 | 9/2020 |
| EP | 3125777 B1 | 9/2020 |
| EP | 3182930 B1 | 9/2020 |
| EP | 3285690 B1 | 9/2020 |
| EP | 3459500 B1 | 9/2020 |
| EP | 3570782 B1 | 9/2020 |
| EP | 3700467 A1 | 9/2020 |
| EP | 3711711 A1 | 9/2020 |
| EP | 3714936 A1 | 9/2020 |
| EP | 2979667 B2 | 10/2020 |
| EP | 3193783 B1 | 10/2020 |
| EP | 3490501 B1 | 10/2020 |
| EP | 3720363 A1 | 10/2020 |
| EP | 2387973 B1 | 11/2020 |
| EP | 2427144 B1 | 11/2020 |
| EP | 2506777 B1 | 11/2020 |
| EP | 2793743 B1 | 11/2020 |
| EP | 2825203 B1 | 11/2020 |
| EP | 2863842 B1 | 11/2020 |
| EP | 2967700 B1 | 11/2020 |
| EP | 2977026 B1 | 11/2020 |
| EP | 3139864 B1 | 11/2020 |
| EP | 3145451 B1 | 11/2020 |
| EP | 3156007 B1 | 11/2020 |
| EP | 3244834 B1 | 11/2020 |
| EP | 3298987 B1 | 11/2020 |
| EP | 3302362 B1 | 11/2020 |
| EP | 3311777 B1 | 11/2020 |
| EP | 3316819 B1 | 11/2020 |
| EP | 3361988 B1 | 11/2020 |
| EP | 3503813 B1 | 11/2020 |
| EP | 3527170 B1 | 11/2020 |
| EP | 3530236 B1 | 11/2020 |
| EP | 3590471 B1 | 11/2020 |
| EP | 3593762 B1 | 11/2020 |
| EP | 3740162 A1 | 11/2020 |
| EP | 2370138 B1 | 12/2020 |
| EP | 2445450 B1 | 12/2020 |
| EP | 2739250 B1 | 12/2020 |
| EP | 2877123 B1 | 12/2020 |
| EP | 2967834 B1 | 12/2020 |
| EP | 2996632 B1 | 12/2020 |

(56) References Cited

FOREIGN PATENT DOCUMENTS

| | | |
|---|---|---|
| EP | 3090703 B1 | 12/2020 |
| EP | 3191025 B1 | 12/2020 |
| EP | 3202371 B1 | 12/2020 |
| EP | 3316822 B1 | 12/2020 |
| EP | 3334382 B1 | 12/2020 |
| EP | 3337424 B1 | 12/2020 |
| EP | 3367896 B1 | 12/2020 |
| EP | 3368582 B1 | 12/2020 |
| EP | 3397208 B1 | 12/2020 |
| EP | 3476366 B1 | 12/2020 |
| EP | 3481303 B1 | 12/2020 |
| EP | 3538028 B1 | 12/2020 |
| EP | 3539510 B1 | 12/2020 |
| EP | 3544548 B1 | 12/2020 |
| EP | 3545906 B1 | 12/2020 |
| EP | 3572117 B1 | 12/2020 |
| EP | 3593763 B1 | 12/2020 |
| EP | 3749254 A1 | 12/2020 |
| EP | 3753535 A1 | 12/2020 |
| EP | 3756623 | 12/2020 |
| EP | 1906883 B1 | 1/2021 |
| EP | 2334261 B1 | 1/2021 |
| EP | 2349096 B1 | 1/2021 |
| EP | 2568924 B1 | 1/2021 |
| EP | 2699202 B1 | 1/2021 |
| EP | 2713894 B1 | 1/2021 |
| EP | 2835112 B1 | 1/2021 |
| EP | 3040054 B1 | 1/2021 |
| EP | 3131502 B1 | 1/2021 |
| EP | 3197397 B1 | 1/2021 |
| EP | 3256178 B1 | 1/2021 |
| EP | 3290007 B1 | 1/2021 |
| EP | 3316821 B1 | 1/2021 |
| EP | 3337412 B1 | 1/2021 |
| EP | 3432834 B1 | 1/2021 |
| EP | 3454786 B1 | 1/2021 |
| EP | 3474778 B1 | 1/2021 |
| EP | 3528748 B1 | 1/2021 |
| EP | 3547966 B1 | 1/2021 |
| EP | 3603576 B1 | 1/2021 |
| EP | 3760164 A1 | 1/2021 |
| EP | 2273951 B1 | 2/2021 |
| EP | 2379008 B1 | 2/2021 |
| EP | 2996641 B1 | 2/2021 |
| EP | 3043747 B1 | 2/2021 |
| EP | 3340936 B1 | 2/2021 |
| EP | 3457985 B1 | 2/2021 |
| EP | 3503847 B1 | 2/2021 |
| EP | 3538027 B1 | 2/2021 |
| EP | 3558168 B1 | 2/2021 |
| EP | 3581232 B1 | 2/2021 |
| EP | 3656354 B1 | 2/2021 |
| EP | 3697324 B1 | 2/2021 |
| EP | 2299938 B1 | 3/2021 |
| EP | 2470121 B1 | 3/2021 |
| EP | 2564811 B1 | 3/2021 |
| EP | 2679198 B1 | 3/2021 |
| EP | 3068346 B1 | 3/2021 |
| EP | 3160394 B1 | 3/2021 |
| EP | 3169245 B1 | 3/2021 |
| EP | 3178443 B1 | 3/2021 |
| EP | 3184081 B1 | 3/2021 |
| EP | 3226956 B1 | 3/2021 |
| EP | 3324892 B1 | 3/2021 |
| EP | 3334354 B1 | 3/2021 |
| EP | 3402446 B1 | 3/2021 |
| EP | 3442469 B1 | 3/2021 |
| EP | 3503851 B1 | 3/2021 |
| EP | 3506855 B1 | 3/2021 |
| EP | 3531979 B1 | 3/2021 |
| EP | 3535010 B1 | 3/2021 |
| EP | 3581151 B1 | 3/2021 |
| EP | 3590472 B1 | 3/2021 |
| EP | 3593760 B1 | 3/2021 |
| EP | 3646825 B1 | 3/2021 |
| EP | 3649985 B1 | 3/2021 |
| EP | 3787561 A1 | 3/2021 |
| EP | 3790501 | 3/2021 |
| EP | 3791795 A1 | 3/2021 |
| EP | 3796873 | 3/2021 |
| EP | 1734872 B1 | 4/2021 |
| EP | 2594230 B1 | 4/2021 |
| EP | 2624785 B1 | 4/2021 |
| EP | 2670349 B1 | 4/2021 |
| EP | 2793752 B1 | 4/2021 |
| EP | 2823769 B1 | 4/2021 |
| EP | 2964152 B1 | 4/2021 |
| EP | 3253331 B1 | 4/2021 |
| EP | 3290004 B1 | 4/2021 |
| EP | 3311778 B1 | 4/2021 |
| EP | 3367979 B1 | 4/2021 |
| EP | 3454794 B1 | 4/2021 |
| EP | 3487420 B1 | 4/2021 |
| EP | 3558165 B1 | 4/2021 |
| EP | 3616651 B1 | 4/2021 |
| EP | 3619136 B1 | 4/2021 |
| EP | 3626208 B1 | 4/2021 |
| EP | 3632379 B1 | 4/2021 |
| EP | 3646823 B1 | 4/2021 |
| EP | 3646824 B1 | 4/2021 |
| EP | 3653173 B1 | 4/2021 |
| EP | 1951155 B1 | 5/2021 |
| EP | 2073755 B1 | 5/2021 |
| EP | 2948100 B1 | 5/2021 |
| EP | 3099270 B1 | 5/2021 |
| EP | 3150172 B1 | 5/2021 |
| EP | 3178445 B1 | 5/2021 |
| EP | 3310301 B1 | 5/2021 |
| EP | 3582697 B1 | 5/2021 |
| EP | 3592295 B1 | 5/2021 |
| EP | 3639888 B1 | 5/2021 |
| EP | 3669828 B1 | 5/2021 |
| EP | 2471492 B1 | 6/2021 |
| EP | 2486894 B1 | 6/2021 |
| EP | 2750630 B1 | 6/2021 |
| EP | 3247312 B1 | 6/2021 |
| EP | 3294215 B1 | 6/2021 |
| EP | 3323353 B1 | 6/2021 |
| EP | 3360513 B1 | 6/2021 |
| EP | 3488821 B1 | 6/2021 |
| EP | 3549555 B1 | 6/2021 |
| EP | 3576677 B1 | 6/2021 |
| EP | 3632338 B1 | 6/2021 |
| EP | 2381895 B1 | 7/2021 |
| EP | 2611389 B1 | 7/2021 |
| EP | 2779945 B1 | 7/2021 |
| EP | 3193740 B1 | 7/2021 |
| EP | 3206629 B1 | 7/2021 |
| EP | 3277222 B1 | 7/2021 |
| EP | 3400907 B1 | 7/2021 |
| EP | 3435919 B1 | 7/2021 |
| EP | 3522800 B1 | 7/2021 |
| EP | 3539508 B1 | 7/2021 |
| EP | 3539509 B1 | 7/2021 |
| EP | 3572044 B1 | 7/2021 |
| EP | 3592289 B1 | 7/2021 |
| EP | 3668450 B1 | 7/2021 |
| EP | 3681439 B1 | 7/2021 |
| EP | 3691567 B1 | 7/2021 |
| EP | 3849472 | 7/2021 |
| EP | 2558032 B1 | 8/2021 |
| EP | 2992857 B1 | 8/2021 |
| EP | 2994075 B1 | 8/2021 |
| EP | 3038539 B1 | 8/2021 |
| EP | 3287099 B1 | 8/2021 |
| EP | 3348235 B1 | 8/2021 |
| EP | 3643273 B1 | 8/2021 |
| EP | 3646822 B1 | 8/2021 |
| EP | 3658215 B1 | 8/2021 |
| EP | 3659553 B1 | 8/2021 |
| EP | 3723665 B1 | 8/2021 |
| EP | 3744290 B1 | 8/2021 |
| EP | 3860530 A1 | 8/2021 |
| EP | 2040645 B1 | 9/2021 |

(56) References Cited

FOREIGN PATENT DOCUMENTS

| | | | |
|---|---|---|---|
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 2358307 | B1 | 12/2021 |
| EP | 2765954 | B1 | 12/2021 |
| EP | 2777608 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3624705 | B1 | 12/2021 |
| EP | 3749254 | B1 | 12/2021 |
| EP | 2400922 | B1 | 1/2022 |
| EP | 2545885 | B1 | 1/2022 |
| EP | 2747708 | B1 | 1/2022 |
| EP | 2763708 | B1 | 1/2022 |
| EP | 2994072 | B1 | 1/2022 |
| EP | 3220856 | B1 | 1/2022 |
| EP | 3288498 | B1 | 1/2022 |
| EP | 3534840 | B1 | 1/2022 |
| EP | 3558169 | B1 | 1/2022 |
| EP | 3668452 | B1 | 1/2022 |
| EP | 3682854 | B1 | 1/2022 |
| EP | 3697346 | B1 | 1/2022 |
| EP | 3700467 | B1 | 1/2022 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | b1 | 2/2022 |
| EP | 2623068 | | 3/2022 |
| EP | 2866737 | | 3/2022 |
| EP | 3160396 | | 3/2022 |
| EP | 3193782 | | 3/2022 |
| EP | 3334380 | | 3/2022 |
| EP | 3355800 | | 3/2022 |
| EP | 3479797 | | 3/2022 |
| EP | 3479800 | | 3/2022 |
| EP | 3628274 | | 3/2022 |
| EP | 3679894 | | 3/2022 |
| EP | 3787561 | | 3/2022 |
| EP | 3791795 | | 3/2022 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920664 | B1 | 9/2010 |
| FR | 2932376 | B1 | 4/2011 |
| FR | 2947716 | B1 | 9/2011 |
| FR | 2945440 | B1 | 12/2012 |
| FR | 2951549 | B1 | 8/2013 |
| FR | 2964855 | B1 | 10/2013 |
| FR | 2977792 | B1 | 10/2013 |
| FR | 2980968 | B1 | 12/2013 |
| FR | 2986149 | B1 | 12/2014 |
| FR | 2997288 | B1 | 1/2015 |
| FR | 2998167 | B1 | 1/2015 |
| FR | 2996747 | B1 | 2/2015 |
| FR | 2996748 | B1 | 2/2015 |
| FR | 3004638 | B1 | 5/2015 |
| FR | 2982763 | B1 | 7/2015 |
| FR | 2991162 | B1 | 7/2015 |
| FR | 3006582 | B1 | 7/2015 |
| FR | 300112181 | | 1/2016 |
| FR | 2998166 | | 2/2016 |
| FR | 3021862 | B1 | 5/2016 |
| FR | 3004917 | B1 | 6/2016 |
| FR | 3006884 | B1 | 6/2016 |
| FR | 3023704 | B1 | 8/2016 |
| FR | 3008885 | B1 | 12/2016 |
| FR | 3033494 | B1 | 3/2017 |
| FR | 3057154 | B1 | 10/2018 |
| FR | 3058631 | B1 | 1/2019 |
| FR | 3058632 | B1 | 1/2019 |
| FR | 3060292 | B1 | 1/2019 |
| FR | 3063631 | B1 | 3/2019 |
| FR | 3020265 | B1 | 9/2019 |
| FR | 3072013 | B1 | 9/2019 |
| GB | 243370 | A | 8/1926 |
| GB | 2407146 | B | 4/2006 |

(56) References Cited

FOREIGN PATENT DOCUMENTS

| GB | 2398245 B | 3/2007 |
|---|---|---|
| GB | 2433700 B | 12/2007 |
| GB | 2478498 B | 7/2012 |
| GB | 2530487 B | 12/2016 |
| GB | 2517609 B | 5/2017 |
| GB | 2538749 B | 8/2017 |
| GB | 2538072 B | 11/2017 |
| GB | 2536538 B | 7/2018 |
| GB | 2548891 B | 7/2018 |
| WO | WO-2018090148 A1 | 5/2018 |

OTHER PUBLICATIONS

"U.S. Appl. No. 15/819,512, Preliminary Amendment filed Nov. 28, 2017", 3 pgs.

"U.S. Appl. No. 15/819,512, Response filed Oct. 28, 2019 to Restriction Requirement dated Aug. 28, 2019", 8 pgs.

"U.S. Appl. No. 15/819,512, Restriction Requirement dated Aug. 28, 2019", 8 pgs.

"International Application Serial No. PCT/CA2017/051387, International Preliminary Report on Patentability dated May 31, 2019", 7 pgs.

"International Application Serial No. PCT/CA2017/051387, International Search Report dated Feb. 2, 2018", 7 pgs.

"International Application Serial No. PCT/CA2017/051387, Written Opinion dated Feb. 2, 2018", 5 pgs.

"Chinese Application Serial No. 2017800720409, Response filed Jun. 1, 2021 to Office Action dated Mar. 1, 2021", w/English claims, 13 pgs.

U.S. Appl. No. 15/819,51, filed Nov. 21, 2017, Methods and Systems for Rapid Retraction of a Transcatheter Heat Valve Delivery System.

"Chinese Application Serial No. 2017800720409, Office Action dated Mar. 1, 2021", with machine translation, 14 pgs.

"European Application Serial No. 17870820.2, Response filed Dec. 18, 2020 to Extended European Search Report dated May 19, 2020", 15 pgs.

"European Application Serial No. 17870820.2, Extended European Search Report dated May 19, 2020", 7 pgs.

"Chinese Application Serial No. 2017800720409, Response filed Jul. 31, 2021 to Telephone Consultation on Jul. 6, 2021", with machine translation and English translation of claims, 56 pgs.

"Australian Application Serial No. 2017361296, First Examination Report dated Apr. 27, 2022", 3 pgs.

"Chinese Application Serial No. 202111153690.0, Voluntary Amendment filed Apr. 13, 2022", w English Claims, 12 pgs.

\* cited by examiner

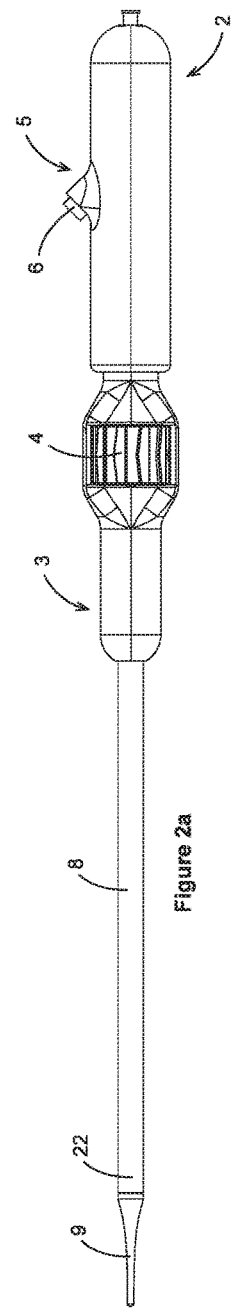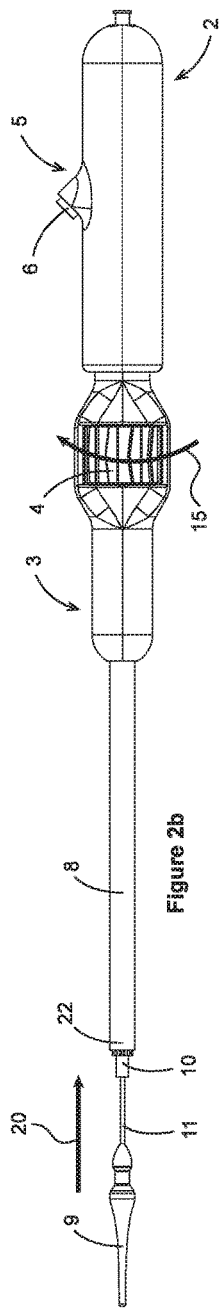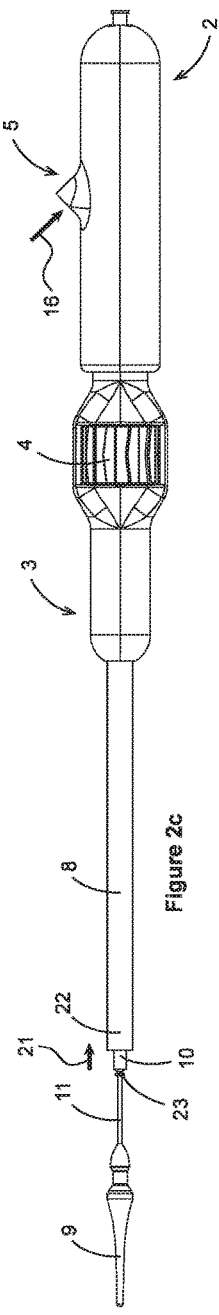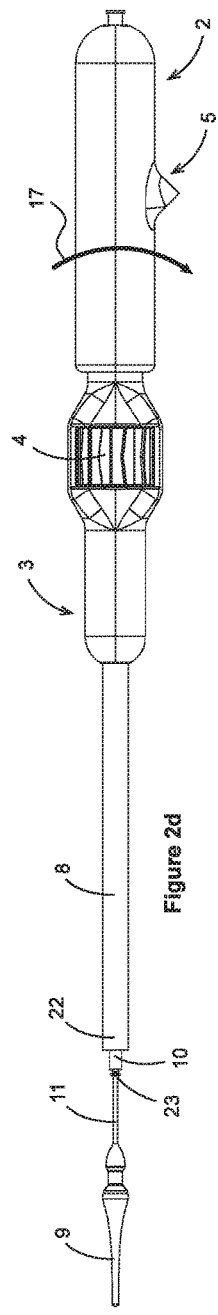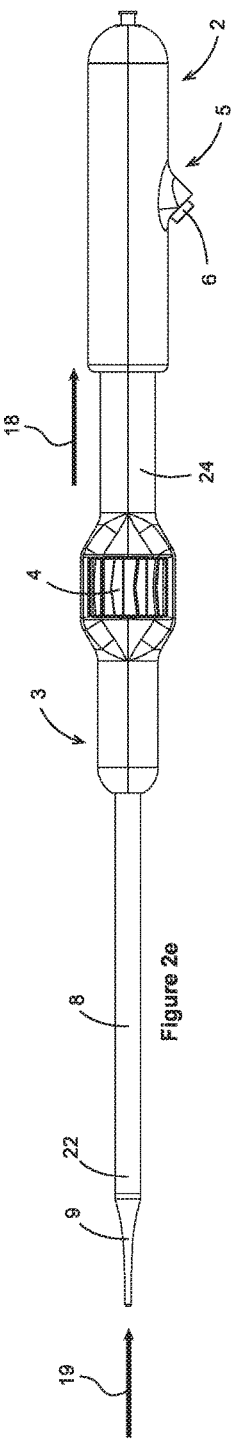

METHODS AND SYSTEMS FOR RAPID RETRACTION OF A TRANSCATHETER HEART VALVE DELIVERY SYSTEM

CROSS-REFERENCE

The present application is a continuation of U.S. patent application Ser. No. 15/819,512, filed Nov. 21, 2017, which application claims priority to U.S. Provisional Patent Application No. 62/424,910, filed on Nov. 21, 2016, which is herein incorporated by reference in its entirety.

The present application is related to: U.S. Pat. No. 8,579,964 filed Apr. 28, 2011; and also related to U.S. Publication Nos. 2013/0211508 filed Nov. 16, 2012; 2014/0052237 filed Feb. 8, 2013; 2014/0155990 filed May 29, 2013; 2014/0257467 filed Mar. 3, 2014; and 2014/0343669 filed Apr. 1, 2014; the entire contents of each of which is incorporated herein by reference.

BACKGROUND OF THE INVENTION

1. Field of the Invention

Mitral regurgitation, also known as mitral insufficiency or mitral incompetence is a heart condition in which the mitral valve does not close properly thereby resulting in abnormal leakage of blood retrograde from the left ventricle through the mitral valve back upstream into the left atrium. Persistent mitral regurgitation can result in congestive heart failure, a costly and often fatal condition. Traditional surgical repair of the valve generally results in a good clinical outcome but requires open heart surgery and a lengthy and costly hospital stay along with an extended recovery period. More recently, minimally invasive procedures have been developed to deliver a prosthetic heart valve percutaneously over a catheter through the patient's vasculature to the heart, or by using a transapical procedure to introduce the prosthesis through the chest wall and through the apex of the heart to the treatment site. An exemplary prosthesis includes any of the embodiments described in U.S. Pat. No. 8,579,964, the entire contents of which are incorporated herein by reference. These prostheses and delivery procedures appear to be promising, but there is yet opportunity to improve procedural outcomes by minimizing the duration of the procedure, from first contact with the delivery system by an operator to final withdrawal of the delivery system and wound closure in the patient. Therefore, it would be desirable to provide improved devices, systems, and methods that reduce the amount of time needed to remove the delivery system from the patient, improve ease of use, speed up the procedure, and reduce risk. At least some of these objectives will be met by the exemplary embodiments described herein.

2. Description of the Background Art

U.S. Pat. No. 8,579,964 discloses an exemplary prosthetic heart valve and trans-catheter delivery system, the entire contents previously incorporated herein by reference.

BRIEF SUMMARY

The present disclosure generally relates to medical systems, devices and methods, and more particularly relates to prostheses and delivery systems such as heart valve delivery systems that may be used to implant a prosthesis such as a valve, including a prosthetic mitral valve, a heart valve, or any other valve. The present disclosure emphasizes exemplary embodiments of a prosthetic mitral valve and delivery system, but one of skill in the art will appreciate that this is not intended to be limiting.

In many embodiments, trans-catheter methods and systems of deploying prosthetic heart valves and rapid retraction of the delivery system are provided. In certain embodiments, the delivery system comprises a trans-apical delivery system that may be used to implant a prosthetic heart valve into anatomical position by way of an incision in the apex of the heart. The trans-apical delivery system may comprise a system of catheters that may be concentrically nested upon one another and that, when combined, may retain a compressed heart valve prosthesis. Removal of the constraint provided by certain catheters may then facilitate deployment of the heart valve prosthesis into the heart. Further embodiments of the trans-apical delivery system that may be used in any of the delivery systems disclose herein may allow for the closure of the delivery catheters at an enhanced speed, such as by way of translation of catheter components within each other in the opposite direction to that required for deployment operation. The operation of such delivery systems may be facilitated through the use of actuator mechanisms such as button mechanisms that may be in communication with linkage systems, or actuator mechanisms such as button mechanisms that may be in communication with flexible members, or even pin coupled components that simplify use.

Further embodiments herein may include delivery systems that allow for alternative implantation pathways such as through the inferior or superior vena cava, the aorta, or the atria.

In an aspect of the present disclosure, a method of rapidly retracting a delivery system comprises providing a delivery system, the delivery system having a plurality of catheters used to deliver a heart valve prosthesis, providing a controllable deployment mechanism, the controllable deployment mechanism having the ability to preferentially release a prosthesis from the catheter, and actuating the controllable deployment mechanism thereby releasing the prosthesis from the catheter. The method may also comprise providing a rapid retraction mechanism, the rapid retraction mechanism having the ability to rapidly close the catheter, actuating the rapid retracting mechanism thereby rapidly closing the catheter.

The method may comprise trans-apically introducing the delivery system into an apex of a heart, or transseptally delivering the delivery system to a heart, delivering the delivery system to the heart via a subclavian vein, delivering the delivery system to the heart via an aorta, or delivering the delivery system to the heart via a left atrium or a right atrium.

Actuating the rapid retraction mechanism may comprise actuating a button and linkage. The rapid retraction mechanism may comprise a threaded region and interference member, and the method may further comprise constraining movement of the rapid retraction mechanism with the threaded region and interference member. The rapid retraction mechanism may comprise a flexible interference member, and the method may further comprise deflecting the flexible interference member. The rapid retraction mechanism may comprise a pin and pin-hole link assembly, and the method may comprise removing the pin from the pin-hole link assembly.

In another aspect of the present disclosure, a delivery device for delivering a prosthesis comprises a first actuation mechanism for controlling movement of a delivery catheter, wherein the delivery catheter may be configured to carry a prosthesis therein, and wherein actuation of the first actuation mechanism may move the delivery catheter away from the prosthesis thereby at least partially removing a constraint therefrom, and a deployment mechanism for controlling release of the prosthesis from an anchoring catheter, the anchoring catheter disposed at least partially in the delivery catheter, and wherein actuation of the deployment mechanism may move the anchoring catheter away from the prosthesis thereby releasing a constraint therefrom. The delivery system may also comprise an inner guidewire catheter having a tapered distal tip, the inner guidewire catheter disposed in the anchoring catheter, and a rapid retraction mechanism for controlling movement of the delivery catheter relative to the tapered distal tip, wherein actuation of the rapid retraction mechanism closes the delivery device such that a proximal end of the distal tip abuts against a distal end of the delivery catheter thereby forming a smooth continuous outer surface of the delivery device.

The actuation mechanism may comprise a thumbwheel. The deployment mechanism may comprise an actuatable button with a linkage coupled thereto. The rapid retraction mechanism may comprise a threaded region and interference member, a flexible interference member, or a pin and pinhole linkage assembly.

In another aspect of the present disclosure, a system for delivering a prosthesis comprise the delivery device described above and a prosthesis such as a prosthetic mitral valve.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 2A-2E illustrate schematic side views of an operational sequence of a trans-apical delivery system configured to allow for rapid retraction.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
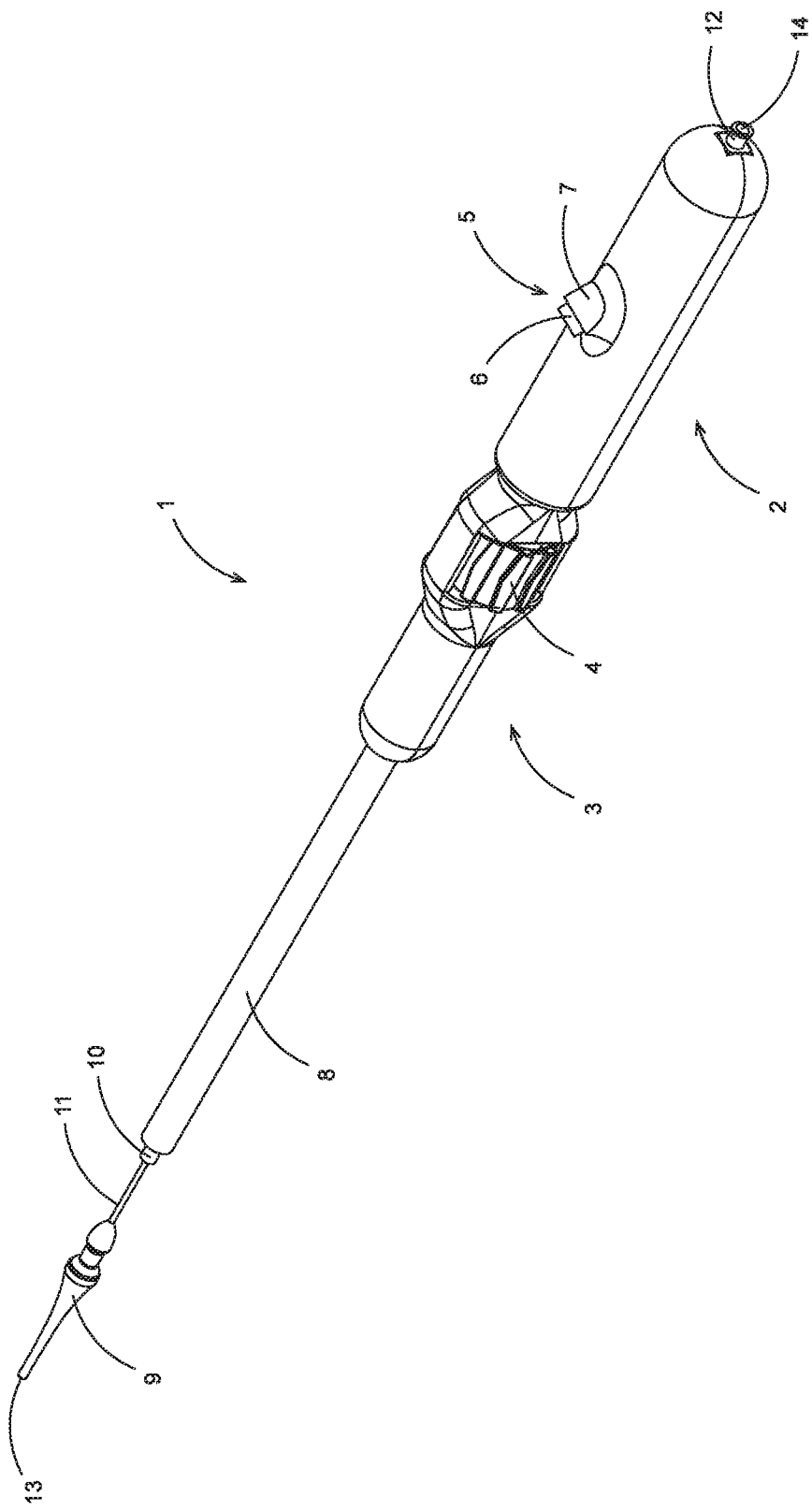
FIG. 1 shows a perspective view of a trans-apical delivery system configured to allow for rapid retraction.

FIG. 1 shows a perspective view of a trans-apical delivery system 1 which may be configured to allow for delivery of a prosthesis such as a prosthetic heart valve with rapid retraction of the delivery system after the prosthesis has been delivered, whereby rapid retraction herein may comprise the expedient removal of the delivery catheter 8 and dilating tip 9 from the apex of a patient's heart (not shown) or other treatment region of the patient. The trans-apical delivery system 1 may be comprised of a dilating tapered tip 9 which is delivered directly into the apex of a patient's heart (not shown), a delivery catheter 8 (sometimes referred to as a sheath catheter), a handle assembly including a distal handle 3, a proximal external handle 2, and an actuator mechanism such as a thumbwheel 4 therebetween which may be configured to actuate said delivery catheter 8 in order to cause it to slidably translate away from the dilating tip 9 into an open configuration or open position. When the trans-apical delivery system is in the open position, a space for a prosthetic heart valve 11 or any other prosthesis may be defined between the dilating tip 9 and the distal edge of the delivery catheter 8 (best seen in FIG. 2A). An innermost lumen can be defined between the guidewire lumen inlet 13, located at the distal most end of the dilating tip 9, and the guidewire lumen outlet 14 which may be located within a connector such as a needle hub 12 having a Luer connector at its proximal end, at the proximal most portion of the proximal external handle 2. The guidewire lumen may extend through the guidewire catheter (sometimes also referred to as the dilator catheter) which may be axially and concentrically disposed under the other catheters including bell catheter 10. The guidewire catheter may be referred to as a guidewire catheter. Any of the features describing the delivery catheter 8 may be applied to any of the delivery catheter embodiments disclosed herein. Similarly, any of the prosthetic heart valve features described for prosthetic heart valve may apply to the prostheses disclosed herein.

Also shown in FIG. 1 is an embodiment of an actuation mechanism 5, which can allow a user to control the final release of a prosthesis such as a prosthetic heart valve from the delivery system, and can enable further mechanical actions that will be described below. The actuation mechanism 5 may be comprised of any actuator such as a button 6, and a disposed in a housing 7 which describes a space wherein the button 6 may translate. The mechanical details behind the translation will be further described below.

Turning now to FIG. 2A-2E, an operational sequence of a trans-apical delivery system 1 configured to allow for rapid retraction is presented. FIG. 2A shows the delivery system 1 in the closed configuration where all catheters may be concentrically disposed over one another, and the distal leading edge 22 of delivery catheter 8 may be disposed against the proximal end of dilating tip 9 to form a smooth continuous outer surface. A prosthesis such as a prosthetic heart valve may be loaded and disposed in the space 11 and constrained by the catheters. The closed configuration may be configured for trans-apical delivery of the prosthesis to the treatment region in the heart. FIG. 2B shows an arrow indicating translation 20 of the distal leading edge of the delivery catheter 22 in the proximal direction. An arrow indicating rotation 15 of the thumbwheel 4 is also shown, and when the thumbwheel 4 is rotated, proximal translation of the distal leading edge of the delivery catheter 8 may occur by way of internal component mechanical relationships, such as those described within U.S. Pat. No. 8,579,964 (also referred to herein as the '964 patent), which is incorporated herein by reference. For example, FIGS. 11-15C of the '964 patent describe one exemplary embodiment of a delivery system having features which may apply to the present exemplary embodiment, and FIGS. 16-20 of the '964 patent describe another exemplary embodiment having features which may apply to the present exemplary embodiment. Rotation of the thumbwheel in the opposite direction may move the delivery catheter 8 in the opposite direction, distally.

FIG. 2C shows an arrow indicating radially inward translation 16 of an actuator, here a button 6. An arrow indicating proximal translation 21 of the distal leading edge 22 of the delivery catheter 8 is also shown, and also when the button 6 is depressed radially inwardly, the leading edge of the bell catheter 10 may translate proximally away from and off of an anchoring catheter (sometimes referred as a hub catheter), anchoring tip 23, as further described in the '964 patent, for example, in FIGS. 16-20. By releasing the leading edge of the bell catheter 10 (similarly referred to as a bell catheter) from the anchoring catheter anchoring tip 23, a prosthesis such as a prosthetic heart valve (not shown) may be preferentially released. The internal mechanics of this component relationship will be further described in detail below.

FIG. 2D depicts the operation of the rapid retraction functionality of the herein disclosed trans-apical delivery system 1. By maintaining pressure on the button 6, the proximal external handle 2 may be rotated as depicted by the arrow indicating rotation 17. By rotating the proximal external handle 2 for one 360° rotation in a first direction (clockwise with respect to the operator), the handle can become disengaged from the middle section of the internal handle 24 and thus may be free to translate proximally over internal handle 24, as depicted by the arrow indicating translation 18 (FIG. 2E). The dilator tip 9 by way of the connector such as needle hub 12 (FIG. 5), and anchoring catheter 50 (FIG. 5) by way of the externally threaded portion of anchoring catheter 51 (FIG. 5) may be mated to the proximal external handle 2. The bell catheter proximal end 68 (FIG. 5) may be fastened to the catheter carriage 30 (FIG. 5), which may be translated along with the proximal external handle 2, and depicted by an arrow indicating translation 19 (FIG. 2E). This movement may allow the proximal end of the dilator tip to butt up against the distal end of the delivery catheter 8 to form a smooth continuous surface when the delivery system is in a closed configuration.

Figure 3A:
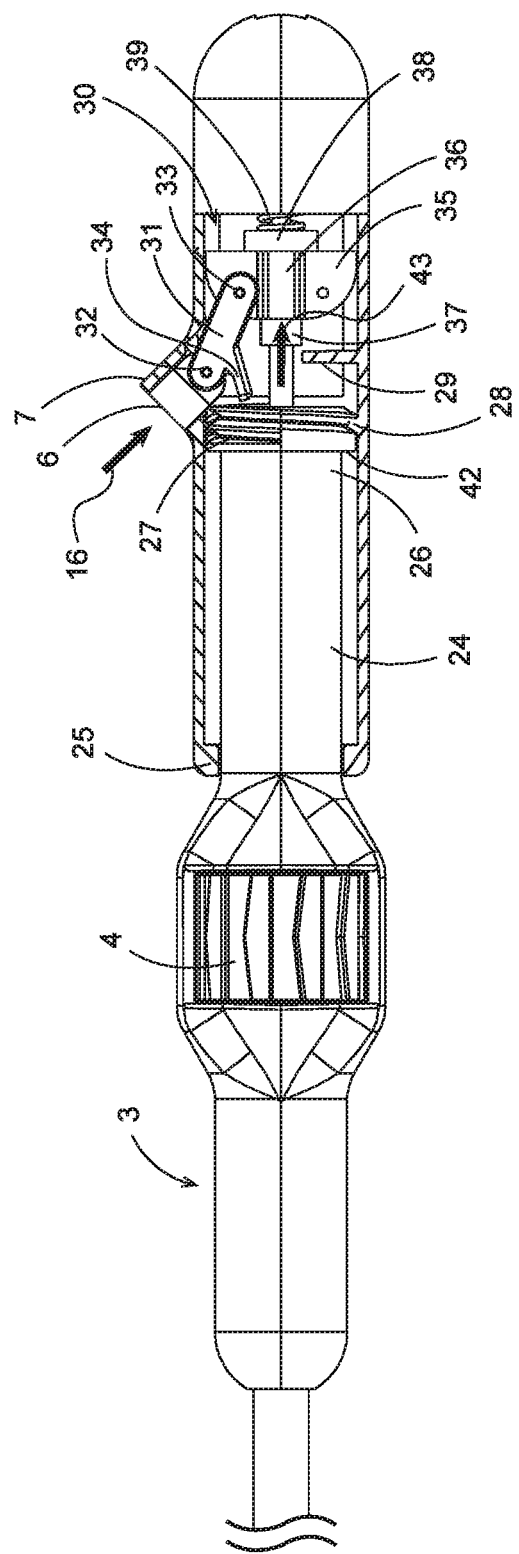
FIGS. 3A-3D illustrate partial cross-sectional breakout views of an operational sequence of a trans-apical delivery system configured to allow for rapid retraction.

FIGS. 3A-3D more clearly illustrate some of the actuation mechanism. Turning now to FIG. 3A, there is illustrated the first view of a sequence of views of an operational sequence of a trans-apical delivery system that is configured to allow for rapid retraction of the delivery system 1, depicted by way of cross-sectional breakout. The middle section of the internal handle 24 is shown, which acts as a support structure for the proximal external handle 2 to slide thereover. Specifically, an internal circular rib 25 may traverse the distal-most portion of the inner diameter of the proximal external handle 2, and in conjunction with the external threads 27 of the middle section of the internal handle 24 as well as an external circular flange 42, may provide support and location for the middle section of the internal handle 24 to translate within the proximal external handle 2 (shown in FIG. 5). In operable communication with the external threads 27 of the middle section of the internal handle 24 may be internal threads 28 of the proximal external handle 2, which can allow for relative rotation and controlled translation between the two handles without binding or cocking, prior to disengagement. An additional feature of embodiments of this device which may be used in any embodiment of a delivery system disclosed herein, with specific regards to the external threads 27 of the middle section of the internal handle 24 is an internal slot 40 (FIG. 4A), the details of which will be described further below.

Figure 4A:
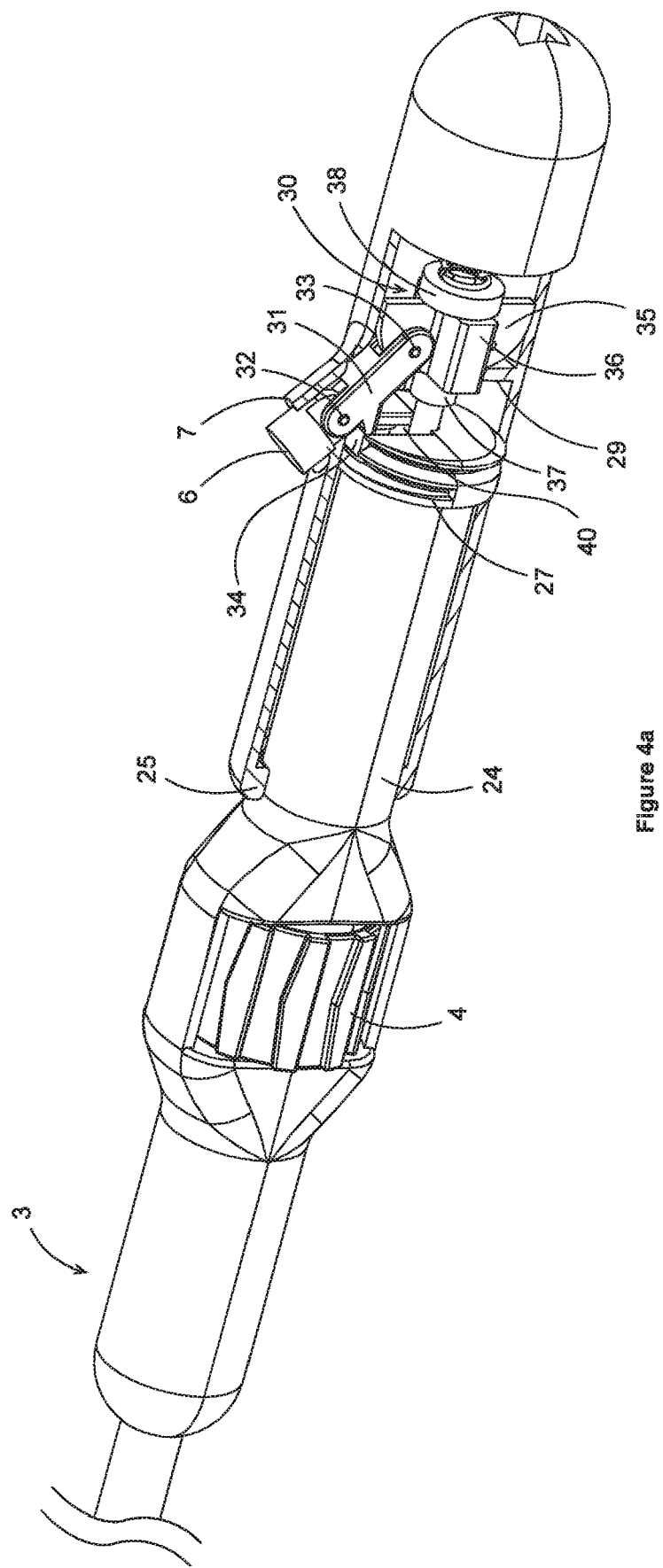
FIGS. 4A-4B illustrate isometric partial cross-sectional breakout views of a sequence of action of an internal mechanism within a trans-apical delivery system configured to allow for rapid retraction.
Figure 4B:
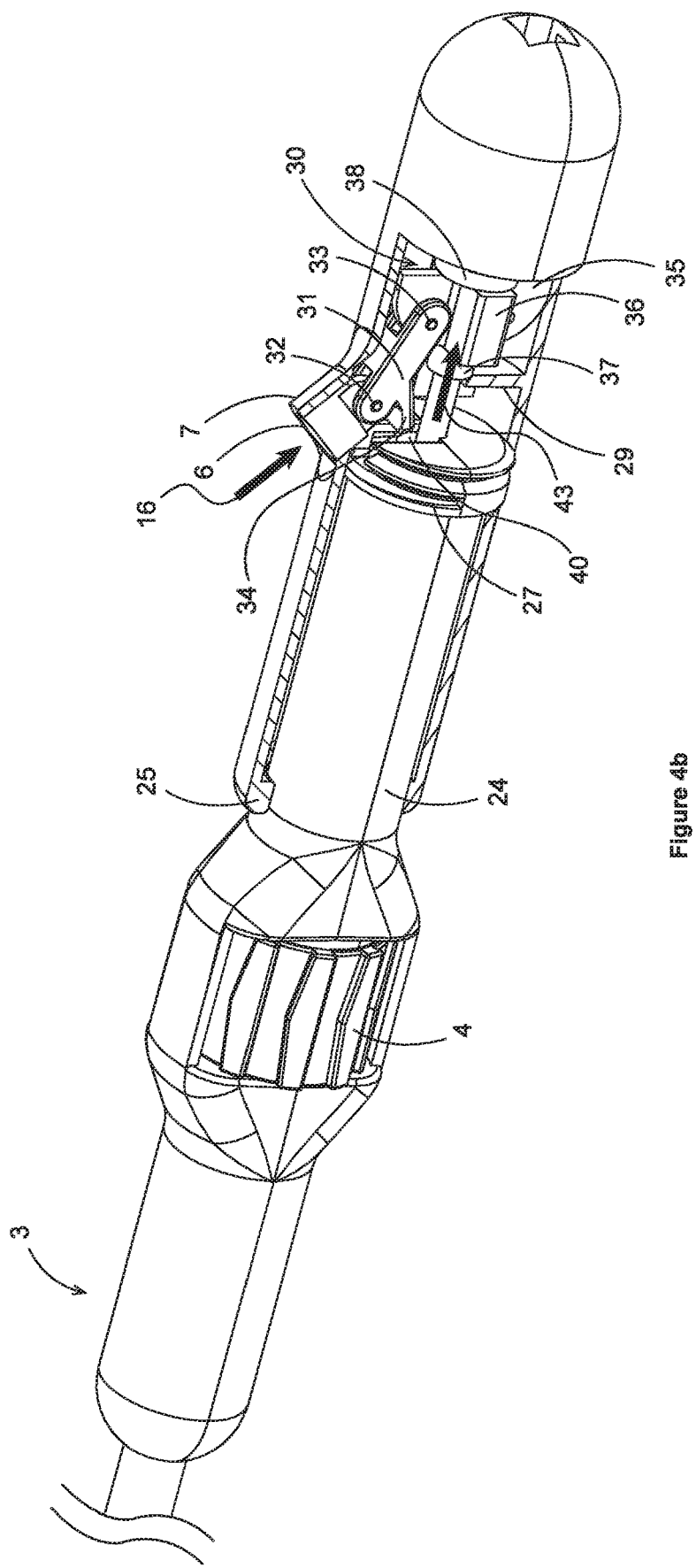
Figure 5:
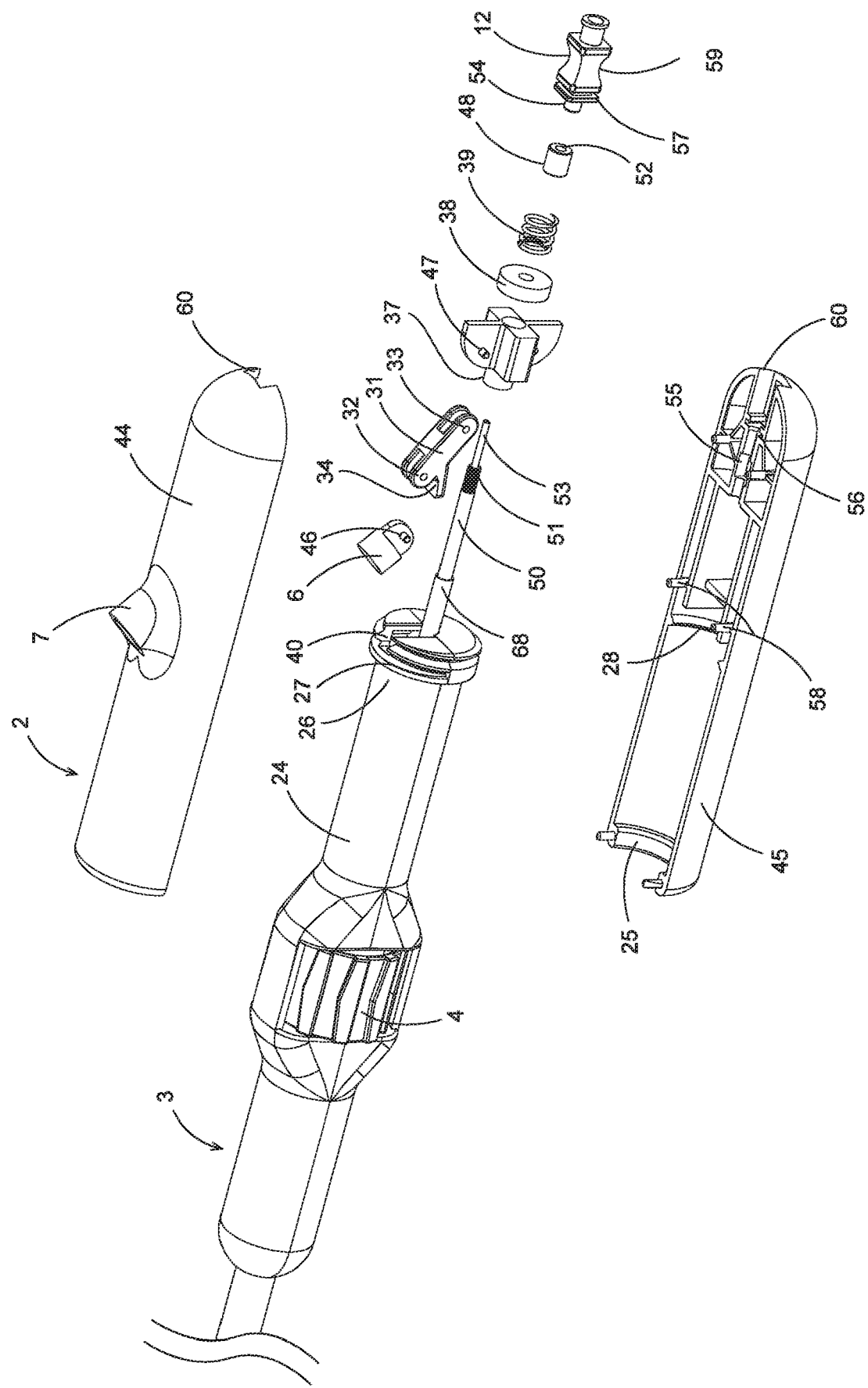
FIG. 5 illustrates an exploded view and internal components of a trans-apical delivery system configured to allow for rapid retraction.

As previously described, a button 6 may be provided which when pushed as depicted by the arrow indicating translation 16 of the button 6, may transmit force and motion along the shaft of the button 6, and through a linkage arm 31, thereby applying it to the catheter carriage 30 and causing it to translate proximally, as depicted by the arrow indicating translation 43 of the catheter carriage 30. Directional control of the translation of the button 6 may be provided by the button housing 7, which may be cylindrically shaped and acts as a piston chamber to guide the similarly cylindrically shaped, piston-like button 6. Functionally, the combination of button 6, linkage arm 31 and catheter carriage 30 may behave as a mechanical linkage. The transmission of force and motion between these components can be achieved through pin-and-hole connection of each successive component to the next; whereas a plurality of button pins 46 (FIG. 5) on one end of the button 6 may be concentrically mated with the distal pin-holes 32 of the linkage arm 31, and a plurality of catheter carriage pins 47 (FIG. 5) on one end of the catheter carriage 30 may be concentrically mated with the proximal pin-holes 33 of the linkage arm 31. The catheter carriage 30 has several characteristics that may assist in its ability to translate smoothly without binding or cocking within the proximal external handle 2. For example, the catheter carriage 30 may have a plurality of support bosses 36 (best seen in FIG. 4A) that can allow the carriage to slide within the proximal external handle 2 by contacting the inner surface of said proximal external handle 2. The catheter carriage 30 may also have a plurality of support fins 35 that can also assist the sliding of the carriage within the proximal external handle 2 by contacting the inner surface of said proximal external handle 2. Additionally, the plurality of support fins 35 may also provide locations for the plurality of catheter carriage pins 47 (FIG. 5).

In order to provide the necessary return force for appropriate valve-capturing ability through the distal end of the bell catheter 10, a cylindrical retaining nut 38 may be in contact with both the catheter carriage 30 and a compression spring 39. This compression spring 39 can act to push the catheter carriage 30 and bell catheter 10 proximal end 68 and distal end towards the dilating tip 9 when the button is released due to the bias provided by the compression spring 39 causing the bell catheter distal end 10 to slide over top of the anchoring catheter anchoring tip 23.

Figure 3B:
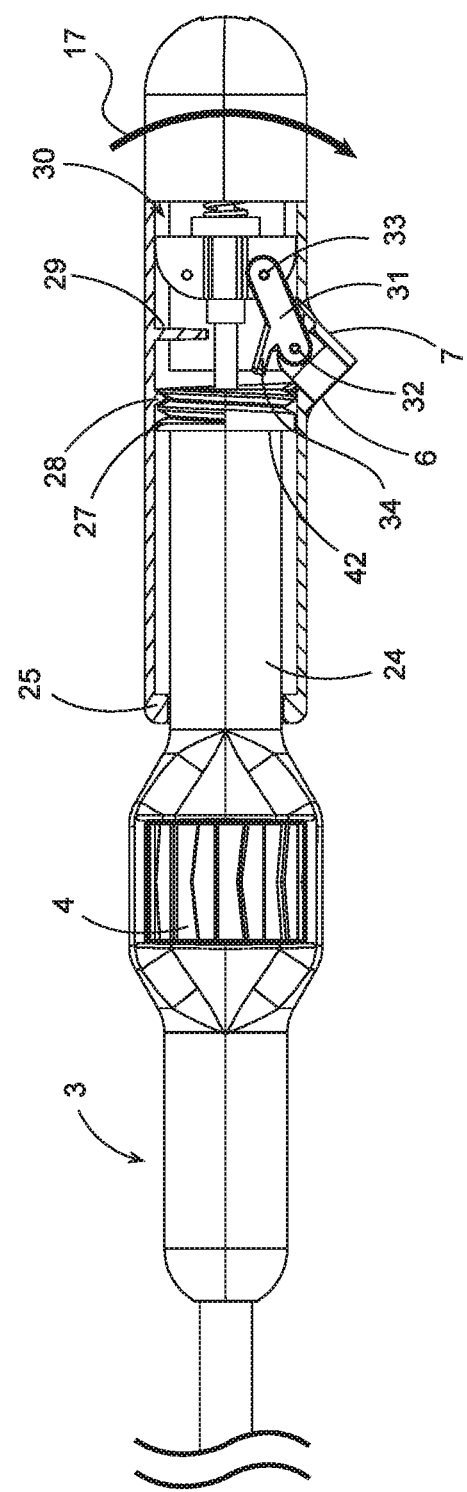
Figure 3C:
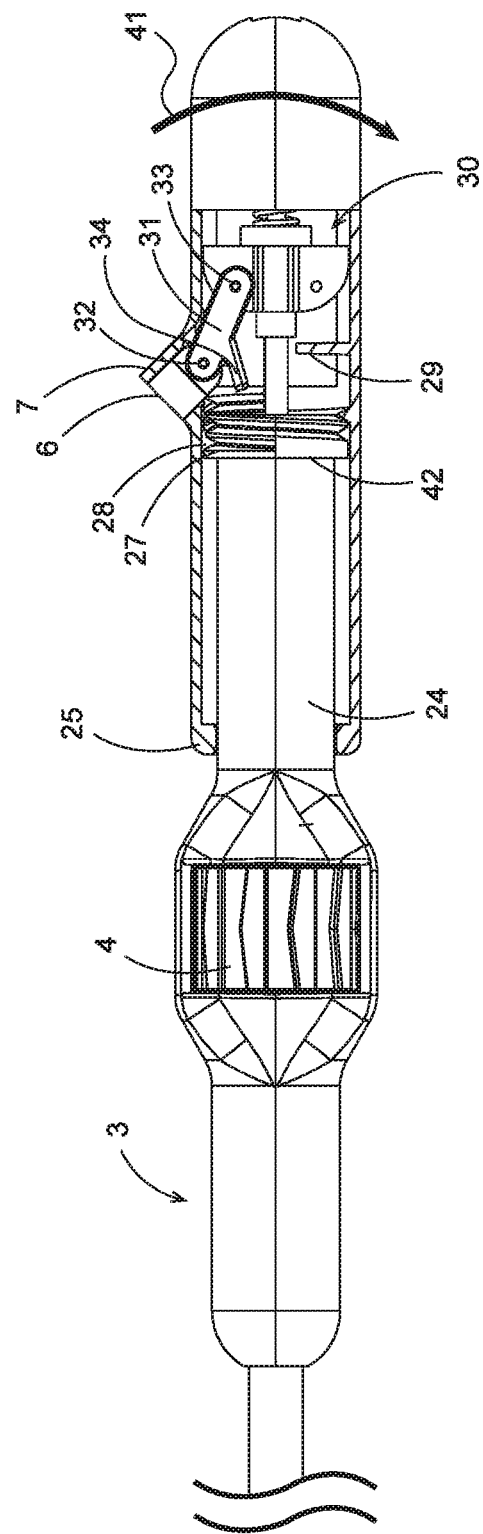
Figure 3D:
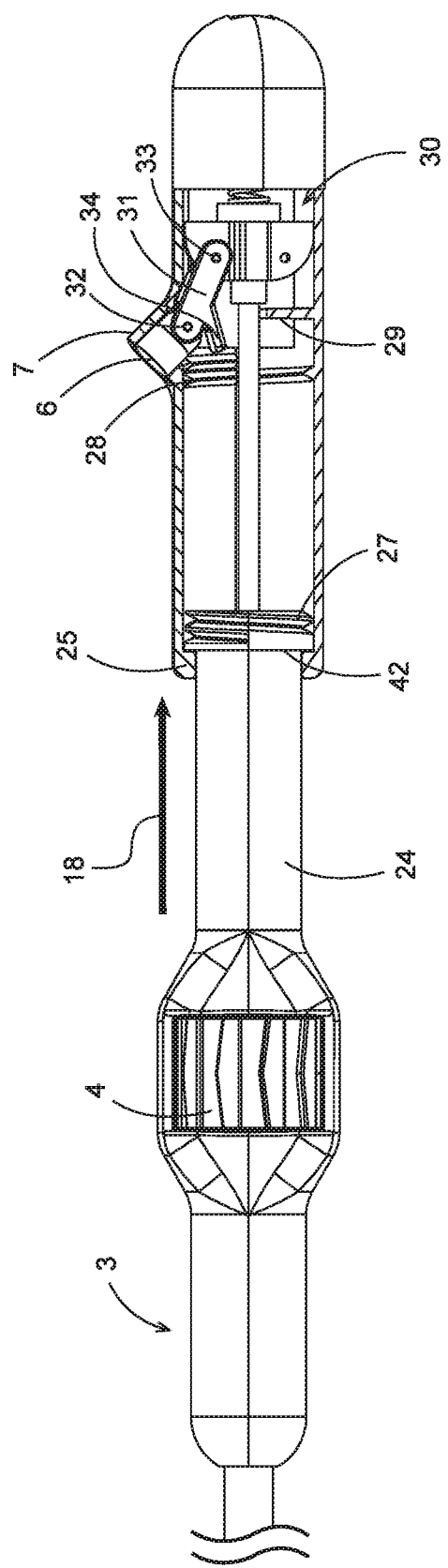

Continuing on through the sequence of views of an operational sequence of a trans-apical delivery system that is configured to allow for rapid retraction of the delivery system 1, by turning to FIG. 3B it is shown that further rotation of the proximal external handle 2 as depicted by the arrow indicating rotation 17, may allow the external threads 27 of the middle section of the internal handle 24 and internal threads 28 of the proximal external handle 2 to further become disengaged. If this rotation is continued (arrow indicating continued rotation 41 of the proximal external handle 2, FIG. 3C), the above mentioned threads may eventually completely disengage, as illustrated in FIG. 3D. Once the above mentioned threads are completely disengaged, the proximal external handle 2 may be free to translate away from the distal handle 3 when pulled proximally by an operator, as depicted by the arrow indicating translation 18 of the proximal external handle 2. The proximal end of the dilator tip may now be butted up against the distal end of the delivery catheter 8 forming a smooth continuous outer surface, and all catheters may be nested within one another. This can complete the rapid retraction process, whereupon the device can safely be removed from the apex of a patient's heart (not shown) or another treatment site. It should be noted that the internal circular rib 25 located on the distal end of the proximal external handle 2 may acts as a rigid, physical stop upon contact with the external circular flange 42 located at the proximal end of the middle section 24 of the internal handle. This limits the translation of the proximal external handle 2 and associated components relative to the internal handle, ensuring the handles do not become fully detached from one another.

As mentioned previously, there is an internal slot 40 (FIG. 4A) located at the proximal-most end of the middle section of the internal handle 24. The purpose of this internal slot 40 is to provide space wherein a rectangular tab 34 of the linkage arm 31 may be placed to prevent unwanted rotation of the proximal external handle 2 relative to the inner handle 24 or distal handle 3, and the relationships between these components is more easily appreciated when witnessed as depicted in FIG. 4A. The rectangular tab may be biased to rest in the slot when the button remains undepressed. One further feature of the mechanical linkage defined by the button 6, linkage arm 31 and catheter carriage 30 that must be appreciated may be realized by the pressing of the button 6, whereupon the rectangular tab 34 of the linkage arm 31 becomes fully removed from the internal slot 40, and full rotation of the proximal external handle 2 relative to the inner handle 24 is thus enabled.

Turning now to FIG. 5, there is illustrated an exploded view with internal components of a trans-apical delivery system configured to allow for rapid retraction of delivery system 1. While many of the elements of FIG. 5 have been previously described herein, additional detail will now be given with emphasis to certain elements used to anchor components within the handle. The proximal external handle 2 may be comprised of two handle halves, specifically an upper section 44 and a lower section 45 which may be fastened together by way of commonly used medical device adhesives such as cyanoacrylate UV cure adhesives that may be applied to a plurality of pegs 58 for mating of said proximal external handle sections 44, 45. Other means for coupling the two handle halves together include but are not limited to press fits, screws, ultrasonic welding, etc. The pegs 58 are illustrated as being located within the lower section 45 of the proximal external handle 2, and each peg may have a complementary boss having an aperture into which it fits in the upper section 44, although it is not shown. The relative positions of the pegs and bosses may be transposed. At the proximal-most end of each of the sections (upper 44, and lower 45) of the proximal external handle 2 there is illustrated a plurality of rectangular slots 60 that may act to securely locate and retain the body 59 of the connector such as needle hub 12. Additionally, a plurality of pockets 56 for retaining the needle hub flange 57 may be provided in close proximity to the plurality of rectangular slots 60, in order to retain and locate a specific fastening feature of the needle hub 12, being primarily the needle hub flange 57. Also found within the upper section 44 and lower section 45 of the proximal external handle 2 may be a plurality of rectangular pockets 55, which serve to locate and retain the anchoring nut 48 and also provide location for an adhesive bond that secures the anchoring nut into the handle sections. It will be remembered that the anchoring nut 48 may provide mechanical fastening and location of the anchoring catheter 50 by way of an externally threaded portion 51 on the anchoring catheter 50 and an internally threaded portion 52 within the anchoring nut 48.

Figure 6:
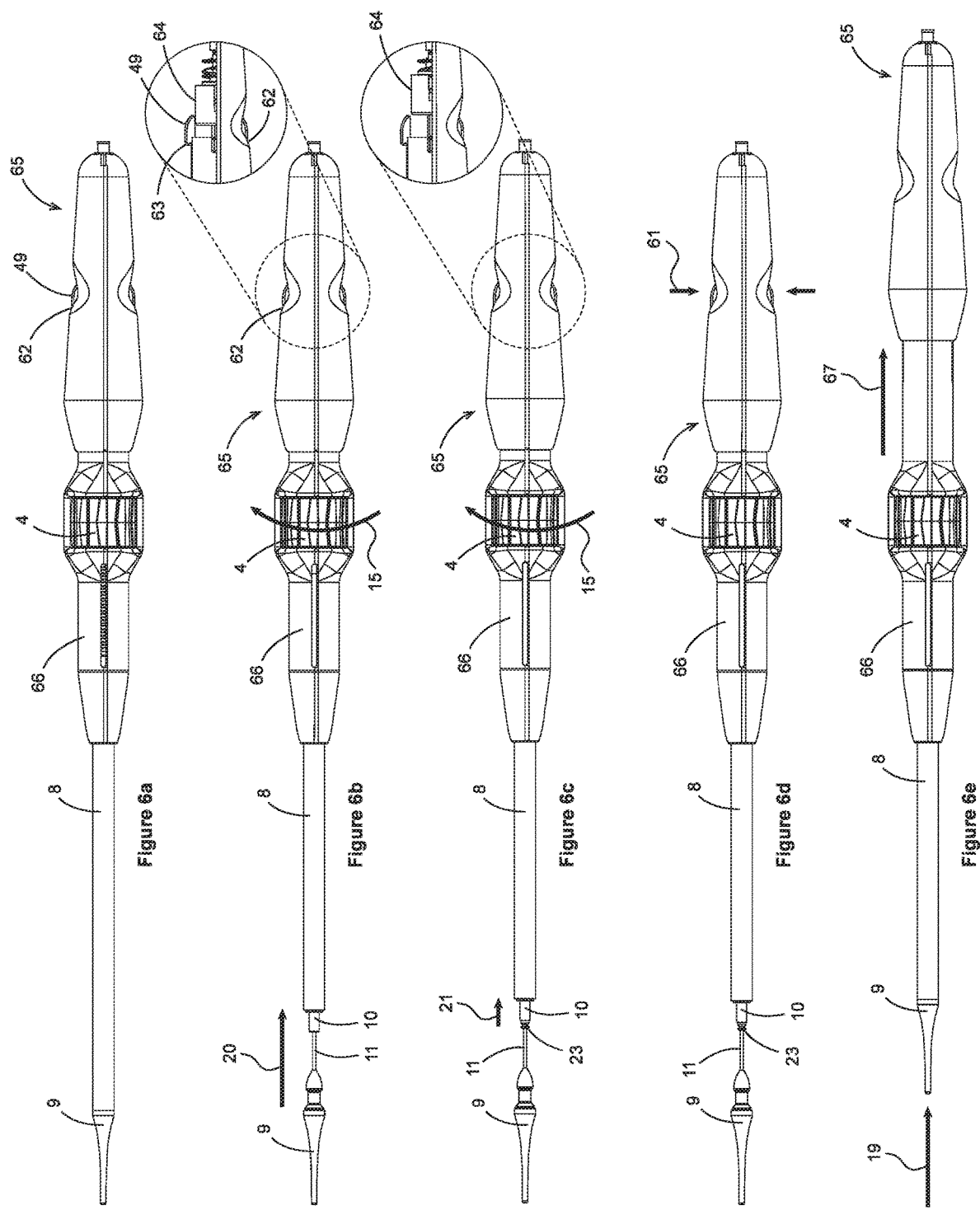
FIGS. 6A-6E illustrate schematic side views of an operational sequence of an alternate embodiment of a trans-apical delivery system configured to allow for rapid retraction.

FIGS. 6A-6E provide illustration of an operational sequence of an alternate embodiment of a trans-apical delivery system 1 configured to allow for rapid retraction. FIG. 6A depicts the first view of an operational sequence, showing another embodiment of a proximal external handle 65. In this embodiment of a proximal external handle 65, rapid retraction may be provided by way of a similar fashion as previously described herein, but with alternative means for disengagement of the proximal external handle 65 from another embodiment of a distal handle section 66. Specifically, the actuator mechanism in this embodiment may include latching buttons 49 (FIG. 6A-6C) which may be used to maintain this embodiment of the distal handle section 66 coupled to this embodiment of the proximal external handle 65. The latching buttons 49 may be in continuous and flexible connection with this embodiment of the distal handle section 66, but may be typically located within a recess of the proximal external handle embodiment 65. Thus, an interfering edge 63 of the latching buttons may be registered against another interfering edge 62 that is within the proximal external handle embodiment 65, prior to engagement. As depicted in FIG. 6D, once both the latching buttons 49 are depressed (illustrated by arrows 61 indicating translation/bending of the cantilevered latching buttons 49) the interfering edge 63 of the buttons may achieve clearance of the interfering edge 62 of the proximal external handle 65 by bending flexion (FIG. 6E). Clearance between the components may allow for translation of this embodiment of the proximal external handle 65 away from this embodiment of the distal handle 66, as depicted by directional arrow 67 indicating translation of the proximal external handle embodiment 65 (FIG. 6E). The remaining internal and external elements of this embodiment (FIG. 6A-6E) of a trans-apical delivery system 1 may be configured to allow for rapid-retraction are as that of the delivery system described in the '964 patent.

Figure 7:
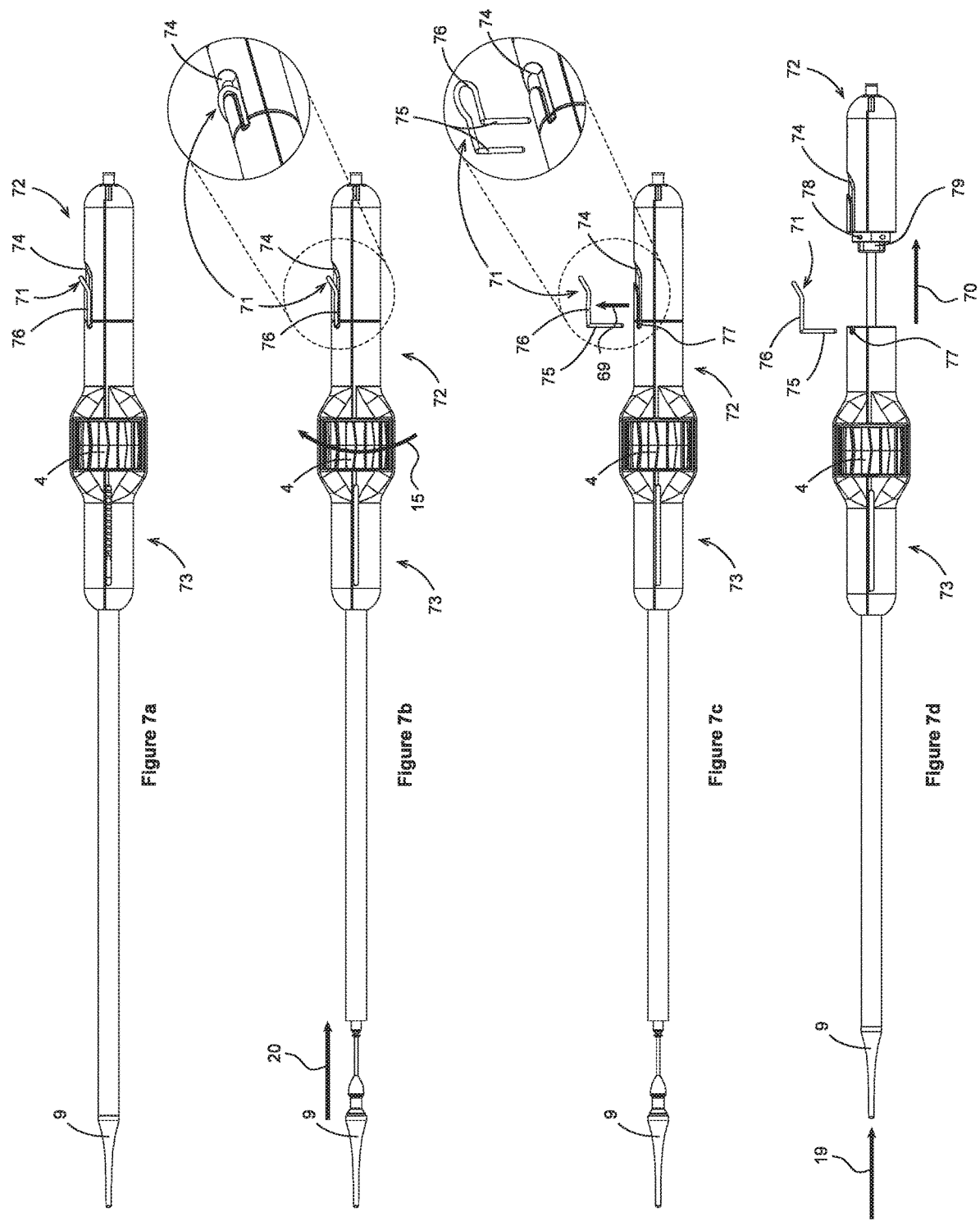
FIGS. 7A-7D illustrate schematic side views of an operational sequence of another alternate embodiment of a trans-apical delivery system configured to allow for rapid retraction.

FIGS. 7A-7D provide illustration of an operational sequence of yet another alternate embodiment of a trans-apical delivery system 1 configured to allow for rapid retraction. FIG. 7A depicts the first view of an operational sequence, showing yet another embodiment of a proximal external handle 72. In this embodiment of a proximal external handle 72, rapid retraction may be provided by way of a similar fashion as previously described herein, but with alternative means for disengagement of the proximal external handle 72 from yet another embodiment of a distal handle section 73. In the embodiment illustrated in FIG. 7A, a retaining pin/latch style of handle retention similar to what may be seen in the modern hand-grenade may be provided. Specifically, a retaining pin 71 which may be comprised of a preferential shaped wire-form having a grasping portion 76 and shafts 75 (FIG. 7C) may be used to pin a proximal external handle section embodiment 72 to a distal handle embodiment 73 by disposing the shafts 75 in receiving pin holes 77 (located on the proximal end of the distal handle embodiment 73) and pin holes 78 (located on the proximal handle embodiment 72). A recess 74 (FIG. 7B) in the handle for the retaining pin 71 may provide a location for the pin to sit flush with the outer surface of the proximal handle embodiment 72, preventing the snagging of sterile gloves that may be adorned by the clinical user (not shown). Operation of the actuation mechanism here having a retaining pin 71 may be as follows: after final deployment of a prosthetic heart valve (not shown) by sustained rotation of the thumbwheel 4 (FIG. 7B), the user may then grasp the retaining pin 71 and pull it out of the recess 74 as depicted by directional arrow 69 indicating translation of the retaining pin 71. Once the retaining pin shafts 75 are entirely removed from the pin holes 77, 78, the proximal external handle embodiment 72 may become free to translate away from the distal handle embodiment 73 as depicted by directional arrow 70 indicating translation of the proximal external handle embodiment 72. The remaining internal and external elements of this embodiment (FIG. 7A-7D) of a trans-apical delivery system 1 may be configured to allow for rapid-retraction are as that of the delivery system described in '964 patent.

Prosthesis

Figure 8:
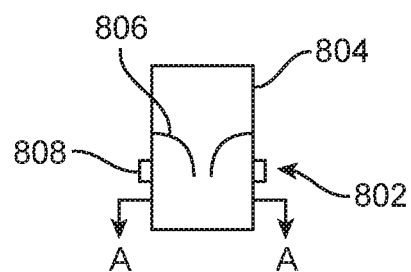
FIG. 8 illustrates a schematic diagram of an exemplary prosthesis

FIG. 8 illustrates a schematic diagram of an exemplary prosthesis 802 which may be used with any of the delivery catheters disclosed herein. The prosthesis 802 is preferably a prosthetic valve such as a prosthetic mitral valve, although it may be a prosthetic valve for any other region in the body such as a prosthetic triscuspid valve, a prosthetic aortic valve, or a prosthetic pulmonary valve. Or it may be a prosthetic venous valve, or any other prosthetic valve, or prosthetic device. The prostheses 802 preferably includes an expandable frame 804 with a prosthetic valve mechanism 806 and preferably includes an anchor mechanism 808. The expandable frame may be balloon expandable or self-expanding and the frame expands into engagement with the native valve. The prosthetic valve mechanism 806 may include one, two, three, or more prosthetic valve leaflets which have an open position which allows antegrade fluid flow therepast, and a closed configuration where the prosthetic valve leaflets coapt with one another to prevent or minimize retrograde fluid flow therepast. The fluid may be blood or another body fluid. The prosthetic leaflets may be pericardial tissue or other tissues, or they may be formed from synthetic materials such as polymers or metals. The anchor mechanism may be any structure configured to help enagage tissue and anchor the prosthesis with the native valve.

Figure 9A:
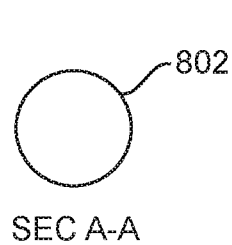
FIGS. 9A-9B illustrate exemplary cross-sections of the prosthesis in FIG. 8.
Figure 9B:
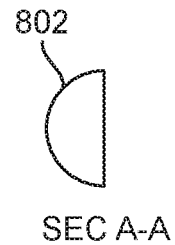

FIGS. 9A-9B illustrates taken along the line A-A in FIG. 8 and show possible cross-sections of the frame 804. FIG. 9A shows that the prosthesis may have a circular cross-section, and in preferred embodiments, preferably for the mitral valve, the prosthesis may have a D-shaped cross-section so that the prosthesis conforms to the native anatomy. Additional details about exemplary embodiments of a prosthesis are disclosed in the '964 patent previously incorporated herein by reference.

Figure 10A:
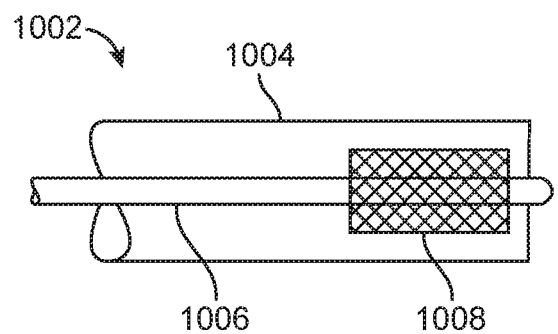
FIGS. 10A-10B illustrate a prosthesis coupled to a delivery catheter.
Figure 10B:
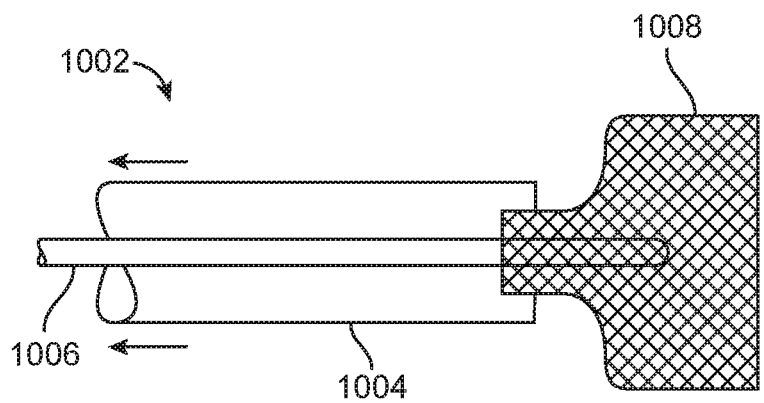

FIGS. 10A-10B illustrate a prosthesis 1008 such as the one described in FIG. 8 coupled to a delivery catheter 1002. In FIG. 10A, the prosthesis is in a collapsed configuration and being carried and constrained by the delivery catheter 1002. The delivery catheter 1002 may be any of the delivery catheters described herein. An outer sheath 1004 constrains the prosthesis 1008 and keeps it in the collapsed configuration and disposed over an inner shaft 1006 slidably disposed in the outer sheath 1004. The inner shaft 1006 may be any of the inner shafts disclosed herein including the bell catheter previously disclosed. Other optional shafts in the delivery catheter are not illustrated for convenience. As the outer sheath 1004 is retracted proximally, or the bell catheter is advanced distally, the prosthesis becomes unconstrained from the outer sheath and begins to self-expand as seen in FIG. 10B. Once the prosthesis is completely unconstrained, is self-expands into position, preferably into engagement with a native valve.

Delivery

Figure 11:
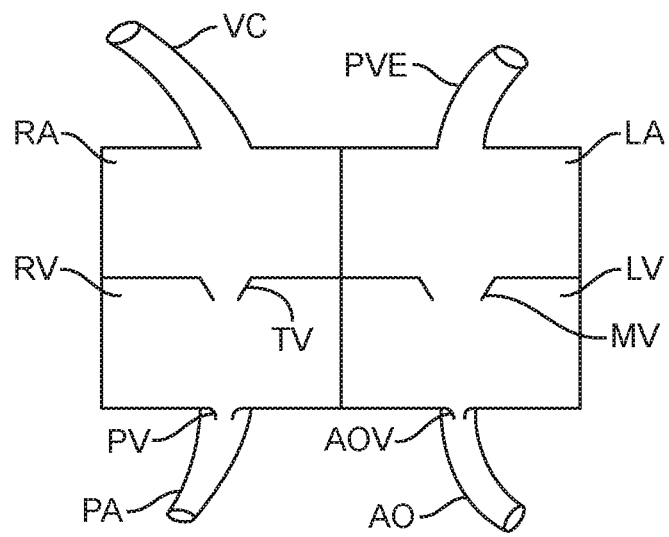
FIG. 11 illustrates basic human heart anatomy.

FIG. 11 illustrates basic human heart anatomy. The heart includes four chambers, the right atrium RA, the right ventricle RV, the left atrium LA, and the left ventricle LV. Several valves prevent retrograde blood flow. The tricuspid valve TV controls flow from the right atrium to the right ventricle, and the pulmonary valve PV controls flow out of the right ventricle RV. The mitral valve MV controls flow between the left atrium LA and the left ventricle LV, and the aortic valve AOV controls flow out of the aorta AO. The major vessels coupled to the heart include the vena cava VC which brings venous blood back to the right atrium RA, and the pulmonary artery brings blood from the right ventricle RV to the lungs (not illustrated). Oxygenated blood from the lungs returns to the left atrium LA via the pulmonary veins PVE, and blood is delivered out of the left ventricle LV to the body by the aorta AO.

Figure 12A:
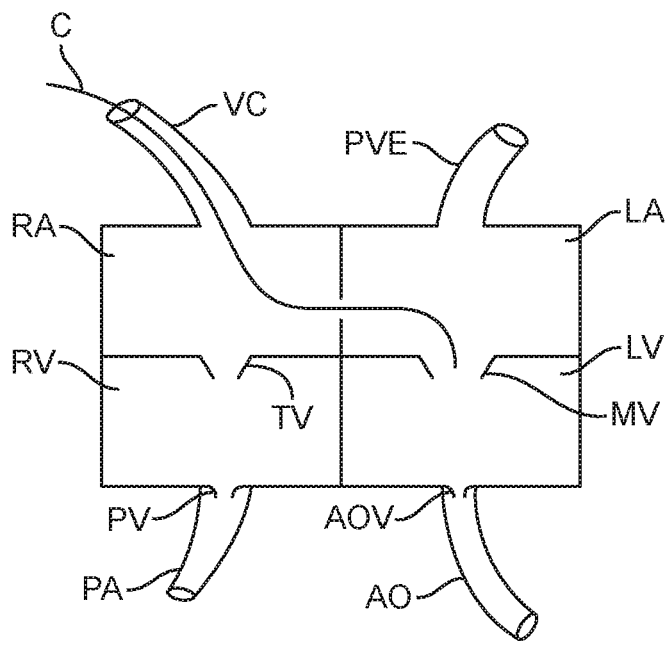
FIGS. 12A-12C illustrate exemplary delivery methods.

FIG. 12A illustrates one exemplary delivery method for treating mitral valve MV. In this embodiment, the delivery catheter C which may be any of the delivery devices disclosed herein and may have any of the prostheses disclosed herein is advanced typically from a femoral vein in the groin up into the vena cava VC into the right atrium RA and then transseptally across the atrial septal wall into the left atrium LA and then downward into disposition across or adjacent the native mitral valve MV where the prosthesis may be deployed as described herein.

Figure 12B:
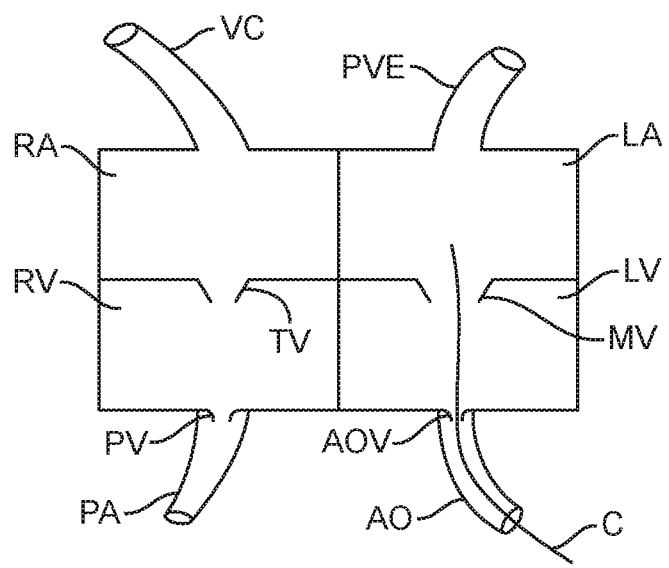

FIG. 12B illustrates another exemplary delivery method for treating a mitral valve MV. In this embodiment, the delivery catheter C which may be any of the delivery devices disclosed herein and may have any of the prostheses disclosed herein is advanced typically from a femoral artery or other artery (e.g. radial artery) up into the aorta AO in to the left ventricle LV and then across the mitral valve MV or adjacent thereto for deployment of the prosthesis as described herein.

Figure 12C:
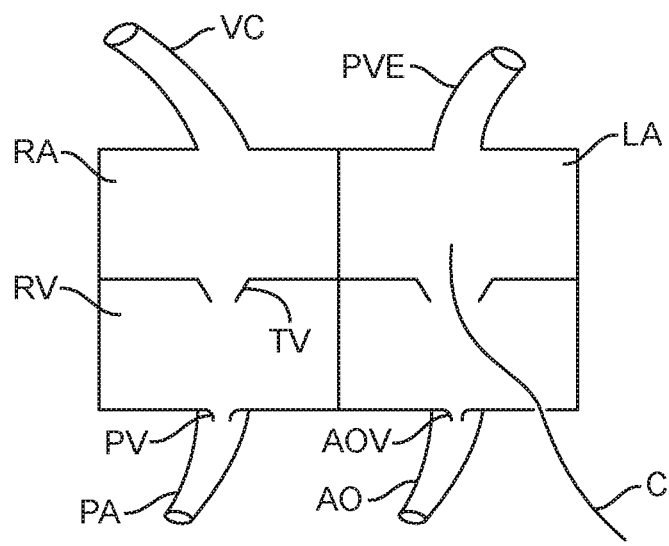

FIG. 12C illustrates another exemplary delivery method for treating a mitral valve MV. In this embodiment, the delivery catheter C which may be any of the delivery devices described herein and may have any of the prostheses disclosed herein is typically advanced transapically from outside the body, through the chest well, into the apex of the heart into the left ventricle LV and then adjacent or across the mitral valve MV where the prosthesis is then deployed as disclosed herein.

Figure 13A:
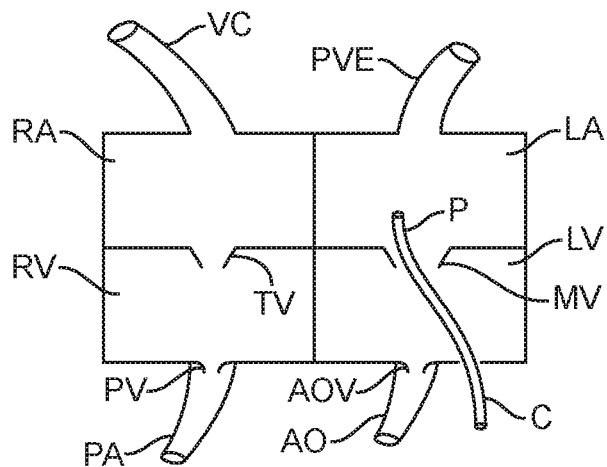
FIGS. 13A-13C illustrate an exemplary method of deploying a prosthesis in the heart.
Figure 13B:
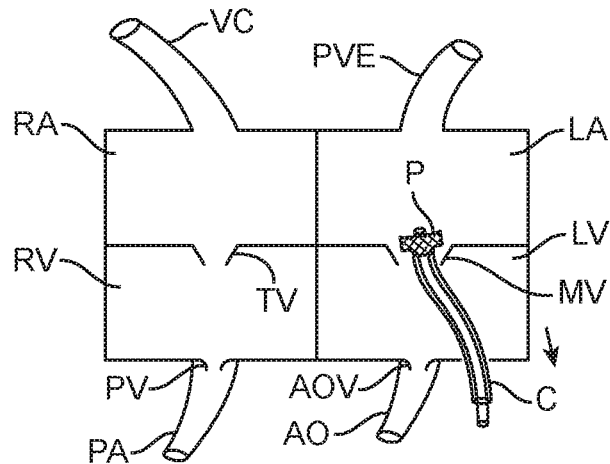
Figure 13C:
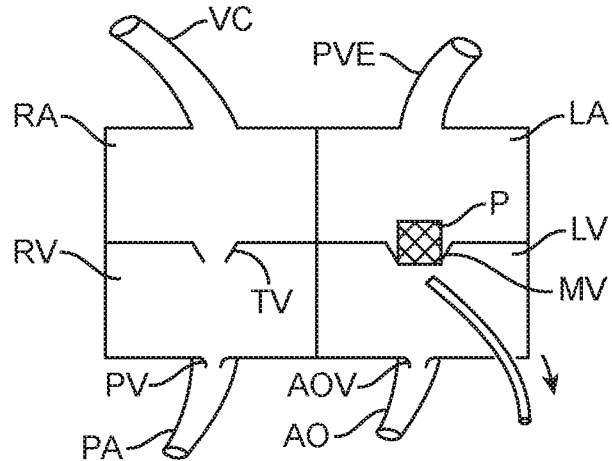

FIGS. 13A-13C illustrate an exemplary method of deploying a prosthesis P in the heart using a delivery catheter C which may be any of the delivery devices disclosed herein. The prosthesis is preferably a mitral valve prosthesis but may be any of the prostheses disclosed herein. In FIG. 13A, the delivery catheter is preferably delivered transapically to the mitral valve MV. In FIG. 13B, once the prosthesis P has been properly positioned relative to the native mitral valve MV, the outer sheath is retracted proximally (or the inner bell shaft is advanced distally) so that the prosthesis is unconstrained and allowed to self-expand into engagement with the native mitral valve and anchor into position. After the prosthetic valve has been deployed and properly positioned and anchored, the delivery catheter is then retracted proximally and removed from the heart as seen in FIG. 13C. The prosthetic valve now takes over the function of the native mitral valve allowing antegrade flow from the left atrium to the left ventricle and preventing or minimizing regurgitation of blood from the left ventricle to the left atrium.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A delivery device for delivering a prosthesis, said device comprising:
   a delivery catheter configured to carry a prosthesis therein;
   a dilator catheter disposed in the delivery catheter, the dilator catheter having a tapered distal tip coupled thereto;
   a rapid retraction mechanism for controlling movement of the delivery catheter relative to the tapered distal tip, wherein actuation of the rapid retraction mechanism closes the delivery device such that a proximal end of the tapered distal tip abuts against a distal end of the delivery catheter, thereby forming a smooth continuous outer surface on the delivery device.

2. The device of claim 1, further comprising a first actuation mechanism for controlling movement of the delivery catheter, wherein actuation of the first actuation mechanism moves the delivery catheter away from the prosthesis thereby at least partially removing a constraint therefrom.

3. The device of claim 2, further comprising a deployment mechanism for controlling release of the prosthesis from an anchoring catheter, the anchoring catheter disposed at least partially in the delivery catheter, and wherein actuation of the deployment mechanism moves the anchoring catheter away from the prosthesis thereby releasing a constraint therefrom.

4. The device of claim 2, wherein the first actuation mechanism comprises a thumbwheel.

5. The device of claim 2, wherein the deployment mechanism comprises an actuatable button with a linkage coupled thereto.

6. The device of claim 1, wherein the rapid retraction mechanism comprises a screw thread and interference member.

7. The device of claim 1, wherein the rapid retraction mechanism comprises a flexible interference member.

8. The device of claim 1, wherein the rapid retraction mechanism comprises a pin and pin-hole linkage assembly.

9. A system for delivering a prosthesis, said system comprising:
   the device of claim 1; and
   the prosthesis.

10. The system of claim 9, wherein the prosthesis comprises a prosthetic mitral valve.

* * * * *